United States Patent [19]

Noe

[11] Patent Number: 4,976,956
[45] Date of Patent: Dec. 11, 1990

[54] METHOD AND COMPOSITION TO IMPART IMPROVED CONDITIONING PROPERTIES TO THE HAIR

[75] Inventor: Jeremy E. Noe, Joliet, Ill.

[73] Assignee: Helene Curtis, Inc., Chicago, Ill.

[21] Appl. No.: 383,729

[22] Filed: Jul. 24, 1989

[51] Int. Cl.$^5$ .............................................. A61K 7/075
[52] U.S. Cl. ..................................... 424/70; 514/772; 514/788; 514/789
[58] Field of Search .................. 424/70; 514/788, 789, 514/772

[56] References Cited

U.S. PATENT DOCUMENTS

| | | | |
|---|---|---|---|
| 4,726,945 | 2/1988 | Patel et al. | 514/938 X |
| 4,777,037 | 10/1988 | Wagman et al. | 424/72 X |
| 4,818,523 | 4/1989 | Clarke et al. | 424/70 |

Primary Examiner—Merrell C. Cashion, Jr.
Assistant Examiner—Susan S. Rucker
Attorney, Agent, or Firm—Marshall, O'Toole, Gerstein, Murray & Bicknell

[57] ABSTRACT

A method of imparting improved conditioning properties to hair comprising treating the hair with a composition comprising a water-soluble quaternary ammonium compound, such as cetrimonium chloride; an oil-soluble, water-dispersible quaternary ammonium compound, such as distearyldimonium chloride; an acid-neutralized amidoamine compound, wherein an amidoamine having the general formula:

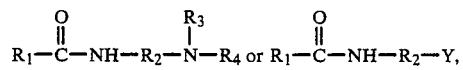

wherein $R_1$ is a fatty acid chain containing from about 11 to about 21 carbon atoms, $R_2$ is an alkylene group containing from two to about four carbon atoms, $R_3$ is hydrogen, methyl, ethyl or a hydroxyalkylene group containing from one to about three carbon atoms, $R_4$ is methyl, ethyl or a hydroxyalkylene group containing from one to about three carbon atoms, and Y is a heterocyclic nitrogen-containing moiety, like morpholine or pyridine, is neutralized with a suitable acid, such as the amidoamine compound stearamidoethylethanolamine neutralized with phosphoric acid; and a low molecular weight polydimethylsiloxane compound, such as cyclomethicone. The method and composition unexpectedly provide improved hair-conditioning properties such as wet feel, wet and dry combing, manageability, sheen, luster, body and overall hair condition.

50 Claims, No Drawings

METHOD AND COMPOSITION TO IMPART IMPROVED CONDITIONING PROPERTIES TO THE HAIR

FIELD OF THE INVENTION

The present invention relates to a hair-treating composition' and to a method of treating hair that unexpectedly imparts improved conditioning properties to hair. More particularly, the present invention is directed to a hair-treating composition comprising at least about 0.35% by weight of a water-soluble quaternary ammonium compound, such as cetrimonium chloride; from about 0.4% to about 15% by weight of an oil-soluble, water-dispersible quaternary ammonium compound, such as distearyldimonium chloride; from about 0.1% to about 5% by weight of an acid-neutralized amidoamine compound, wherein an amidoamine compound having the general structural formula (I) or (II):

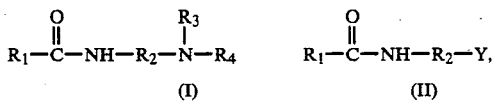

wherein $R_1$ is a fatty acid chain containing from about 11 to about 21 carbon atoms, $R_2$ is an alkylene group containing from two to about four carbon atoms, $R_3$ is hydrogen, methyl, ethyl or a hydroxyalkylene group containing from one to about three carbon atoms, $R_4$ is methyl, ethyl or a hydroxyalkylene group containing from one to about three carbon atoms, and Y is a heterocyclic nitrogen'-containing moiety, like morpholine or pyridine, is neutralized with a suitable acid, such as the amidoamine compound stearamidoethylethanolamine neutralized with phosphoric acid; and from about 0.1% to about 2% by weight of a low molecular weight polydimethylsiloxane compound, such as cyclomethicone. The composition of the present invention can be applied to the hair from an aqueous or nonaqueous solution or spray, an emulsion, a conditioner formulation, a hair color and/or other similar hair treatment products, over a pH range of from about 4 to about 7, to improve both the wet stage and the dry stage properties of the hair.

BACKGROUND OF THE INVENTION

Most individuals buy and use a hair shampoo for its cleansing properties. In addition to having clean hair, the consumer also desires sufficiently-conditioned hair that holds a preset configuration. However, hair shampoos generally are formulated with highly effective synthetic surfactants, like anionic surfactants, that primarily clean as opposed to conditioning the hair. Therefore, shampoos usually neither aid in the detangling of wet hair nor impart any residual conditioning benefits to dry hair, such as manageability or styleability of hair sets.

Consequently, the hair normally is left in a cosmetically-unsatisfactory state after washing with an anionic surfactant-based hair shampoo Anionic surfactants not only remove the dirt and soil from the hair, but also remove essentially all of the sebum naturally present on the surface of the hair fibers. Therefore, it was found that the desirable properties of anionic surfactants that effectively clean the hair also serve to leave the hair in a cosmetically-unsatisfactory condition. In general, hair shampoo compositions containing anionic surfactants, or non-ionic surfactants or amphoteric surfactants, leave the hair with an undesirable harsh, dull and dry touch, or feel, usually called "creak", after the hair is shampooed and then rinsed with water.

Furthermore, thoroughly cleansed hair also is extremely difficult to comb, in either the wet or the dry state, because the individual hair fibers tend to snarl, kink, and interlock with each other. In addition, incompletely dried hair, such as hair dried with a towel, has poor brushing properties, and after complete drying, the hair does not set well. Furthermore, the combing or brushing property of the hair remains poor, and the hair has undesirable electrostatic properties in a low humidity atmosphere that causes the hair to "fly away", thereby further reducing the brushing properties of the hair. The unsatisfactory combing or brushing property of hair immediately after shampooing, or during trimming treatments after shampooing, also causes hair damage, such as split ends or hair breakage In addition, the natural luster and resiliency of the hair is reduced. Consequently, the overall unsatisfactory condition of the shampooed hair usually necessitates a subsequent post-shampoo treatment of the hair with a special conditioning composition to improve these undesirable physical characteristics. These conditioning compositions normally are applied separately from the hair shampoo, and usually are rinses or cream-like lotions containing a cationic compound Therefore', consumer needs traditionally have been met by the application of a shampoo to cleanse the hair, followed by the application of a conditioner composition to improve wet combing. The commonly accepted method has been to shampoo the hair, followed by rinsing the hair, and then separately applying a conditioner composition, followed by a second rinse. As previously discussed, freshly shampooed hair is inclined to knot and tangle, and therefore is difficult to comb and difficult to manage. The wet combing problem has been solved by treating shampooed hair with a conditioner composition that coats the hair shaft and causes the individual hair shafts in a tress to resist tangling and matting because of the conditioner residue retained on the shaft.

However, the need for improved compositions that condition the hair, i.e., renders the hair more manageable, has long been recognized in the art. As previously discussed, it is well-known that anionic surfactants are suitable for hair shampooing, and that cationic compounds, like cationic surfactants and cationic polymers, are useful as hair conditioners. Therefore, cationic compounds that are substantive to hair usually are used to complete the hair cleansing and hair conditioning cycle. The ability of cationic compounds to adsorb or react with the keratinous material of the hair makes them the most desirable compounds for imparting the desired improvement in wet hair detangling and dry hair manageability. However, hair conditioning compositions including cationic compounds that adsorb particularly strongly to the hair also can reduce the elasticity, body and set of the dried hair. Therefore, although conditioning compositions for application to freshly shampooed hair are well known, new and improved conditioning formulations based on cationic compounds are continually sought. Consequently, the present invention is directed to a new hair conditioning composition comprising a combination of suitable hair-conditioning ingredients that improve the wet combing and dry combing properties of hair and also leaves the dry hair with satisfactory cosmetic properties and physical properties, including, in particular, elasticity, manageability, body, sheen and set.

Hair conditioning compositions, such as creme rinses, are well known in the art for improving the combing properties of wet hair and dry hair. These conditioning compositions typically are aqueous emulsions including a cationic compound, like a quaternary ammonium compound, as the principal conditioning agent. The prior art describes the quaternary ammonium compound either as a polymeric material having a plurality of quaternary nitrogen atoms per molecule or as a molecule having at least one long carbon atom chain and an average of one quaternary nitrogen atom per molecule. The prior art also describes hair conditioning compositions as including silicon-containing compounds, substituted amines and amides, non-ionic surfactants, long carbon chain alcohols, and other ingredients to facilitate composition formulation and enhance consumer appeal For example, U.S. Pat. No. 3,993,744 to Cella et al discloses that cationic compounds, such as quaternary ammonium compounds, and silicones can be combined with perfluorinated compounds to provide hair treatment compositions. The silicones specifically disclosed by Cella et al are surfactant-like polyoxyethylene polymethylsiloxanes that are presumed to be water-soluble or dispersible. According to Cella et al, both the quaternary ammonium compounds and the silicones are utilized in relatively small amounts, e.g., about 0.05 weight percent of the composition. Other prior art patents disclosing the use of silicones having viscosities greater than about 100 centistokes at 25° C. to provide lubricity or sheen to various cosmetic preparations, include U.S. Pat. Nos. 2,942,008; 3,594,409; 3,824,303; and 4,014,995.

British Pat. No. 1,598,567 further discloses the use of linear or cyclic, volatile polydimethylsiloxanes, i.e., having a boiling point in the range of 99° C. to 265° C., in hair conditioning compositions. The composition of British Pat. No. 1,598,567 is described as avoiding the formation of an oleophilic hair surface that usually occurs when using a quaternary ammonium hair conditioning agent South African patent application 666,421 also teaches the use of compositions containing straight chain and volatile cyclic silicone fluids to provide gloss and conditioning effects to hair dressings.

Nachtigal et al, in U.S. Pat. No. 4,275,055, discloses a pearlescent hair conditioner composition including a quaternized tertiary amidoamine, a quaternary ammonium compound and, optionally, a tertiary amidoamine, i.e., stearamidoethyldiethylamine. The composition of Nachtigal et al is directed to achieving a stable pearlescent effect and includes neither the low molecular weight polydimethylsiloxane nor the combination of a water-soluble quaternary ammonium compound and an oil-soluble quaternary ammonium compound of the present invention.

Bolich et al, in U.S. Pat. No. 4,374,825, discloses an aqueous hair conditioning composition comprising a volatile hydrocarbon or volatile silicone, a cationic hair conditioning agent and a non-ionic thickening agent. Similarly, Bolich et al in U.S. Pat. No. 4,472,375, discloses a hair conditioning composition comprising a volatile hydrocarbon or a volatile silicone, a non-ionic thickening agent, a quaternary ammonium salt and a salt of a fatty amine. Neither Bolich et al patent teaches or suggests using a combination of an oil-soluble cationic hair conditioning agent with a water-soluble cationic hair conditioning agent, together with a volatile polydimethylsiloxane and an amidoamine compound to provide the hair conditioning composition of unexpected efficacy of the present invention. Bolich, in U.S. Pat. No. 4,387,090, also discloses a hair conditioner composition comprising a volatile hydrocarbon or a volatile silicone conditioning agent and a hydrophobic thickening agent. Other prior art references relating to the use of a volatile agent in hair conditioning compositions include U.S. Pat. Nos. 3,577,528; 3,932,610; and 3,818,105.

Japanese TKS 57-50909 discloses a hair conditioner composition comprising a volatile silicone and a combination of two quaternary ammonium salts, wherein each quaternary ammonium salt includes two long chain alkyl groups. As required by Japanese TKS 57-50909, both quaternary ammonium salts are oil-soluble, wherein the first quaternary ammonium salt includes two alkyl groups each of 16 to 18 carbon atoms, and the second quaternary ammonium salt includes two alkyl groups each of 20 to 22 carbon atoms. Consequently, neither quaternary ammonium salt of Japanese TKS 57-50909 is water soluble, as required by the composition and method of the present invention. Furthermore, Japanese TKS 57-50909 does not teach or suggest using an acid-neutralized amidoamine compound in a composition to impart unexpected hair conditioning properties to hair.

Wagman et al in U.S. Pat. No. 4,777,037 discloses a hair conditioner composition comprising a polydimethyl cyclosiloxane, a sole quaternary-nitrogen containing conditioning agent having two long alkyl chains of twelve to eighteen carbons and two short alkyl chains of one or two carbon atoms, a long chain fatty alcohol and a tertiary amidoamine of the general structural formula (III):

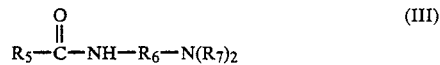

$$R_5-\overset{\overset{\displaystyle O}{\|}}{C}-NH-R_6-N(R_7)_2 \qquad (III)$$

wherein $R_5$ is a fatty chain having from about 11 to about 17 carbon atoms, $R_6$ is an alkylene group having 2 or 3 carbon atoms and $R_7$ is either methyl or ethyl. Wagman et al specifically teaches against using a combination of a water-soluble quaternary ammonium compound and an oil-soluble quaternary ammonium compound in a composition to achieve the improved conditioning properties of the present invention.

As will be demonstrated more fully hereinafter, and in contrast to prior art hair conditioning compositions, a hair conditioner composition of the present invention, comprising a water-soluble quaternary ammonium compound, an oil-soluble quaternary ammonium compound, a low molecular weight polydimethylsiloxane and an acid-neutralized amidoamine compound of general structural formula (I) or (II), unexpectedly imparts improved conditioning properties upon application to human hair Therefore, in accordance with the present invention, hair conditioning properties are surprisingly and unexpectedly improved by a method of contacting the hair with a composition comprising a water-soluble quaternary ammonium compound, an oil-soluble quaternary ammonium compound, a low molecular weight polydimethylsiloxane and an acid-neutralized amidoamine compound of general structural formula (I) or (II). The compositions of the present invention can be applied to the hair from an aqueous or a nonaqueous, such as alcoholic, vehicle at ambient temperature and are allowed to contact the hair for relatively short times to provide the benefits and advantages of a hair conditioner. Consequently, the method and composition of the present invention condition the hair to provide more manageable and esthetically-pleasing hair.

SUMMARY OF THE INVENTION

In brief, the present invention relates to a composition and method of treating hair. More particularly, the present invention relates to a method of treating the hair, whereby the hair is conditioned by contacting the hair with a composition comprising a water-soluble quaternary ammonium compound; an oil-soluble, water-dispersible quaternary ammonium compound; a low molecular weight polydimethylsiloxane compound; and an acid-neutralized amidoamine compound, wherein the amidoamine compound has the general structural formula (I) or (II):

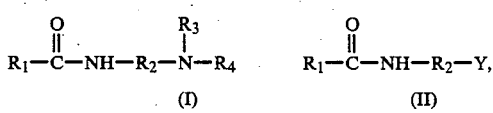

wherein $R_1$ is a fatty acid chain containing from about 11 to about 21 carbon atoms, $R_2$ is an alkylene group containing from two to about four carbon atoms, $R_3$ is hydrogen, methyl, ethyl or a hydroxyalkylene group containing from one to about three carbon atoms, $R_4$ is methyl, ethyl or a hydroxyalkylene group containing from one to about three carbon atoms, and Y is a heterocyclic nitrogen-containing moiety. The easy-to-apply composition imparts excellent wet stage and excellent dry stage conditioning properties to the hair. Surprisingly and unexpectedly, hair treated with a composition of the present invention also demonstrates improved physical properties and cosmetic properties, such as gloss, thickness, manageability, softness and body.

Therefore, it is an object of the present invention to provide a hair-treating composition that conditions the hair and imparts improved physical properties and cosmetic properties to the hair.

It is also an object of the present invention to provide a hair-treating composition comprising a water-soluble quaternary ammonium compound; an oil-soluble, water-dispersible quaternary ammonium compound; a low molecular weight polydimethylsiloxane compound; and an acid-neutralized amidoamine compound having general structural formula (I) or (II).

Another object of the present invention is to provide a hair-treating composition that is capable of conditioning the hair and imparting improved physical and cosmetic properties to the hair over a pH range of about 4 to about 7.

Another object of the present invention is to provide a method of treating hair with a hair-treating composition to achieve an improved condition of the hair.

Another object of the present invention is to provide a method of treating hair by contacting the hair with a composition having a pH of between about 4 and about 7 and comprising a water-soluble quaternary ammonium compound, an oil-soluble quaternary ammonium compound, a low molecular weight polydimethylsiloxane compound and an acid-neutralized amidoamine of general structural formula (I) or (II); then drying the hair, to condition the hair and to impart improved physical and cosmetic properties to the hair.

Another object of the present invention is to provide a method of treating hair to yield unexpectedly well conditioned hair by contacting the hair with a composition comprising at least about 0.35% by weight of a water-soluble quaternary ammonium compound; from about 0.4% to about 15% by weight of an oil-soluble, water-dispersible quaternary ammonium compound; from about '0.1% to about 2% by weight of a low molecular weight polydimethylsiloxane compound; and from about 0.1% to about 5% by weight of an acid-neutralized amidoamine compound having the general structural formula (I) or (II).

Another object of the present invention is to provide a method of treating hair to yield unexpectedly well conditioned hair by contacting the hair with a composition comprising at least about 0.35% by weight cetrimonium chloride; from about 0.4% to about 15% by weight of distearyldimonium chloride; from about 0.1% to about 2% by weight of cyclomethicone; and from about 0.1% to about 5% by weight of phosphoric acid-neutralized stearamidoethylethanolamine, an amidoamine compound of general structural formula (I) having the structural formula (IV):

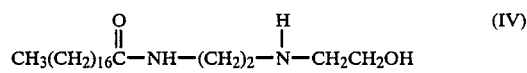

Another object of the present invention is to provide a new and improved hair conditioning composition capable of conditioning the hair and imparting improved physical, cosmetic and esthetic properties both to normal hair and to tinted, frosted, bleached or other substantially-damaged hair.

Still another object of the present invention is to provide a method of treating the hair to yield unexpectedly well conditioned hair having esthetically-pleasing physical properties by contacting the hair with an aqueous or non-aqueous, i.e., alcoholic, spray, solution or emulsion to treat the hair, without heat, in either a rinse-off or leave-on method.

DETAILED DESCRIPTION OF THE PREFERRED EMBODIMENT

The hair-conditioning composition of the present invention comprises a water-soluble quaternary ammonium compound; an oil-soluble, water-dispersible quaternary ammonium compound; a low molecular weight polydimethylsiloxane compound; and an acid-neutralized amidoamine compound In accordance with an important feature of the present invention, the acid-neutralized amidoamine compound is an amidoamine compound having the general structural formula (I) or (II):

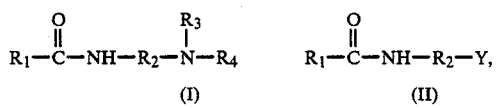

wherein $R_1$ is a fatty acid chain containing from about 11 to about 21 carbon atoms, $R_2$ is an alkylene group containing from two to about four carbon atoms, $R_3$ is hydrogen, methyl, ethyl or a hydroxyalkylene group containing from one to about three carbon atoms, $R_4$ is methyl, ethyl or a hydroxyalkylene group containing from one to about three carbon atoms, and Y is a heterocyclic nitrogen-containing moiety, like morpholine or pyridine, neutralized with a suitable acid. The easy-to-apply composition provides excellent wet comb and excellent dry comb properties to the hair, and the hair demonstrates improved physical and cosmetic properties, such as gloss, thickness, softness, manageability and body.

The water-soluble quaternary ammonium compounds useful in the composition of the present invention are water-soluble quaternary ammonium compounds having one or two long chain alkyl groups containing from about 8 to about 18 carbon atoms. The long chain alkyl groups also can include, in addition to, or in replacement of, carbon and hydrogen atoms, ether linkages or similar water-solubilizing linkages. The remaining two or three substituents of the quaternary nitrogen of the quaternary ammonium compound can be hydrogen; or benzyl; or short chain alkyl or hydroxyalkyl groups, such as methyl, ethyl, hydroxymethyl or hydroxyethyl groups; or combinations thereof, either of the same or of different identity, as long as the quaternary ammonium compound is water soluble. Therefore, the water-soluble quaternary ammonium compound can be depicted by the following general structural formula:

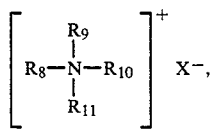

wherein $R_8$ is an alkyl group including from about 8 to about 18 carbon atoms; $R_9$ is selected from the group consisting of an alkyl group including from about 8 to about 18 carbon atoms, a hydrogen atom, a methyl group, an ethyl group, a hydroxymethyl group and a hydroxyethyl group; $R_{10}$ is selected from the group consisting of a benzyl group, a hydrogen atom, a methyl group, an ethyl group, a hydroxymethyl group and a hydroxyethyl group; $R_{11}$ is selected from the group consisting of a hydrogen atom, a methyl group, an ethyl group, a hydroxymethyl group and a hydroxyethyl group; and X is selected from the group consisting of chloride, methosulfate, ethosulfate and nitrate. However, it should be noted that the quaternary nitrogen of the water-soluble quaternary ammonium compound also can be included in a heterocyclic nitrogen-containing moiety, such as morpholine or pyridine. Furthermore, the anion of the quaternary ammonium compound can be any common anion, in addition to those listed above, such as bromide, tosylate, acetate, or phosphate, as long as the quaternary ammonium compound is water soluble.

As previously discussed, water-soluble quaternary ammonium compounds are well-known hair conditioners. The quaternary ammonium salts are substantive to the hair and provide some of the properties desired in well-conditioned hair. Consequently, several water-soluble quaternary ammonium compounds have been found useful as hair conditioning agents, and therefore can be used as the water-soluble quaternary ammonium compound component in the composition and method of the present invention.

The water-soluble conditioning agents having a quaternary nitrogen atom and one or two long alkyl chains including from about 8 to about 18 carbon atoms per molecule include a broad range of compounds. However, the water-soluble conditioning agents generally can be divided into groups based upon the structure of the substituents present on the quaternary nitrogen atom, i.e., (a) compounds having one or two long alkyl chains and one, two or three hydrogen atoms or identical or different short chain alkyl or hydroxyalkyl groups containing one or two carbon atoms, i.e., methyl, ethyl, hydroxymethyl or hydroxyethyl groups; (b) compounds having one or two long alkyl chains, one benzyl group and one or two hydrogen atoms or identical or different short chain alkyl or hydroxyalkyl groups having one or two carbon atoms; and (c) compounds having one long alkyl chain, and one organic heterocyclic nitrogen-containing moiety, like morpholine or pyridine, and none or one hydrogen atom or a short chain alkyl or hydroxyalkyl group having one or two carbon atoms. Although both polymeric water-soluble quaternary ammonium compounds, i.e., compounds having more than one quaternary ammonium nitrogen per molecule, and water-soluble quaternary ammonium compounds including one quaternary ammonium nitrogen per molecule can be used in the composition and method of the present invention, the quaternary ammonium compounds including one quaternary ammonium nitrogen are preferred because they do not impart a greasy feel to the hair.

Therefore, in accordance with an important feature of the present invention, a water-soluble quaternary ammonium compound is hereby further defined as a compound, that, when mixed with water, forms a true solution such that the quaternary ammonium compound, when present up to its saturation point, will not separate from the water phase. Consequently, the following water-soluble quaternary ammonium compounds are exemplary, but not limiting, of water-soluble quaternary ammonium compounds that can be used in the method and composition of the present invention:

| | |
|---|---|
| Lauryltrimethylammonium chloride | (Laurtrimonium chloride); |
| Stearyltri(2-hydroxyethyl) ammonium chloride | (Quaternium-16); |
| Lauryldimethylbenzyl-ammonium chloride | (Lauralkonium chloride); |
| Oleyldimethylbenzyl-ammonium chloride | (Olealkonium chloride); |
| Dilauryldimethylammonium chloride | (Dilauryldimonium chloride); |
| Cetyldimethylbenzylammonium chloride | (Cetalkonium chloride); |
| Dicetyldimethylammonium chloride | (Dicetyldimonium chloride); |
| Laurylpyridinium chloride | (Laurylpyridinium chloride); |
| Cetylpyridinium chloride | (Cetylpyridinium chloride); |
| N-(soya alkyl)-N,N,N-trimethyl ammonium chloride | (Soyatrimonium chloride); |
| Polydiallyldimethyl-ammonium chloride | (Polyquaternium-6); |
| Diallyldimethyl ammonium salt copolymerized with acrylamide | (Polyquaternium-7); |
| Guarhydroxypropyltrimonium chloride | (Guarhydroxypropyltrimonium chloride |
| Copolymer of N-vinyl-pyrrolidone and N,N-dimethylaminoethyl methacrylate, quaternized with dimethylsulfate | (polyquaternium-11); |
| Copolymer of acrylamide and N,N-dimethylaminoethyl methacrylate, | (Polyquaternium-5); |

| -continued | |
|---|---|
| quaternized with dimethyl sulfate | |
| Cationic hydroxyethylcellulosics | (Polyquaternium-10); |
| Cationic hydroxyethylcellulosics | (Polyquaternium-24); |
| Cetyltrimethylammonium chloride | (Cetrimonium chloride); |
| Decyldimethyloctylammonium chloride | (Quaternium-24); |
| Myristyltrimethylammonium chloride | (Mytrimonium chloride); |
| Polyoxyethylene (2)-cocomonium chloride | (PEG-2 Cocomonium chloride); |
| Methylbis(2-hydroxyethyl)cocoammonium chloride | (PEG-2 Cocoyl Quaternium-4); |
| Methylpolyoxyethylene-(15) cocoammonium chloride | (PEG-15 Cocoyl Quaternium-4); |
| Methylbis(2-hydroxyethyl)octadecyl ammonium chloride | (PEG-2 Stearyl Quaternium-4); |
| Methylpolyoxyethylene-(15) octadecylammonium chloride | (PEG-15 Stearyl Quaternium-4); |
| Methylbis(2-hydroxyethyl)-oleylammonium chloride | (PEG-2 Oleyl Quaternium-4); |
| Methylpolyoxyethylene-(15) oleylammonium chloride | (PEG-15 Oleyl quaternium-4); | wherein the name in parenthesis is the compound name given by the Cosmetic, Toiletry and Fragrance Association, Inc. in the *CTFA Cosmetic Ingredient Dictionary*, 3rd ed., 1982, hereinafter referred to as the *CTFA Dictionary*.

It should be noted that a long alkyl chain of the water-soluble quaternary ammonium compound does not have to be solely, or primarily, of one chain length, i.e., the long chain need not be only lauryl ($C_{12}$) or myristyl ($C_{14}$). Rather, a quaternary ammonium compound wherein the long alkyl chain is a mixture of lengths can be used, as long as the quaternary ammonium compound is water soluble. SUch conditioning agents are prepared conveniently from naturally-occurring materials, such as tallow, coconut oil, soya oil and the like, or from synthetically produced mixtures Examples of water-soluble quaternary ammonium compounds having mixed carbon chain lengths include N-(soyaalkyl)-N,N,N-trimethyl ammonium chloride (soyatrimonium chloride) and polyoxyethylene(2-)cocomonium chloride (PEG-2 cocomonium chloride).

The water-soluble quaternary ammonium compound is included in the hair conditioner composition of the present invention in an amount of at least about 0.35% by weight of the composition. Preferably, the water-soluble quaternary ammonium compound is present in an amount ranging from about 0.35% to about 5% by weight of the composition, and to achieve the full advantage of the present invention, the water-soluble quaternary ammonium compound is present in an amount ranging from about 0.35% to about 3% by weight of the composition. As will be discussed more fully hereinafter, it has been found that amounts of water-soluble quaternary ammonium compound of at least about 0.35% by weight are necessary to provide hair conditioning compositions of the present invention that impart an unexpectedly high degree of hair conditioning to treated hair.

In accordance with another important feature of the present invention, in addition to the water-soluble quaternary ammonium compound, the hair conditioner composition also includes from about 0.4% to about 15% of an oil-soluble, water-dispersible quaternary ammonium compound. To achieve the full advantage of the present invention, the oil-soluble, water-dispersible quaternary ammonium compound is present in the composition in an amount ranging from about 0.4% to about 7% by weight of the composition. Similar to the water-soluble quaternary ammonium conditioning agent, the oil-soluble, water-dispersible quaternary ammonium conditioning agents also are known ingredients for use in hair conditioner compositions. Consequently, several oil-soluble, water-dispersible quaternary ammonium compounds are available for use in the method and composition of the present invention.

An oil-soluble, water-dispersible quaternary ammonium compound useful in the composition of the present invention is a quaternary ammonium compound having one or two long chain alkyl groups including from about 14 to about 22 carbon atoms. The remaining two to three substituents present on the quaternary nitrogen of the quaternary ammonium compound can be hydrogen; or benzyl; or short chain alkyl groups, such as methyl, or ethyl; or combinations thereof, as long as the quaternary ammonium compound is oil soluble and water dispersible. Therefore, the oil-soluble quaternary ammonium compound can be depicted by the following general structural formula:

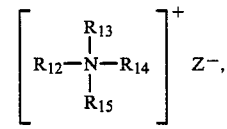

wherein $R_{12}$ is an alkyl group including from about 14 to about 22 carbon atoms; $R_{13}$ is selected from the group consisting of an alkyl group including from about 14 to about 22 carbon atoms, a methyl group and an ethyl group; $R_{14}$ is selected from the group consisting of a benzyl group, a methyl group and an ethyl group; $R_{15}$ is selected from the group consisting of a methyl group and an ethyl group; and Z is selected from the group consisting of chloride, bromide, methosulfate, ethosulfate, tosylate, acetate, nitrate and phosphate. However, it should be noted that the quaternary nitrogen of the oil-soluble quaternary ammonium compound can be included in a heterocyclic nitrogen-containing moiety such as pyridine or morpholine The anion of the oil-soluble quaternary ammonium compound can be any common anion, such as chloride, bromide, methosulfate, ethosulfate, tosylate, acetate, phosphate or nitrate, as long as the quaternary ammonium compound is oil soluble. It should be noted that, in certain instances, it is the anionic portion of the quaternary ammonium compound that determines whether the quaternary ammonium compound is water soluble or oil soluble. For example, in comparing the quaternary ammonium compounds cetyltrimethylammonium chloride (cetrimonium chloride), cetyltrimethylammonium bromide (cetrimonium bromide) and cetyltrimethylammonium p-toluenesulfonate (cetrimonium tosylate), the cations of the quaternary ammonium compounds are identical. However, cetrimonium chloride is water soluble, whereas cetrimonium bromide and cetrimonium tosylate are oil soluble. Therefore, a change in identity of the anion can effectively change the solubility characteristics of the quaternary ammonium compound.

In addition, other seemingly minor variations in molecular structure can significantly effect the solubility characteristics of a quaternary ammonium compound. For example, dramatic effects are demonstrated by varying the carbon chain length of the long alkyl chain of the quaternary ammonium compound. In general, the water solubility of the quaternary ammonium compound decreases as the carbon chain length of the long alkyl chain of a quaternary ammonium compound increases. Consequently, cetyldimethylbenzylammonium chloride (cetalkonium chloride) is water soluble, whereas the addition of two carbon atoms renders the resulting stearyldimethylbenzylammonium chloride (stearalkonium chloride) water insoluble and oil soluble.

Furthermore, the degree of unsaturation, i.e., the presence of carbon-carbon double bonds, in the long alkyl chain of the quaternary ammonium compound can affect the water-solubility of the compound. For example, the quaternary ammonium compounds stearyldimethylbenzylammonium chloride (stearalkonium chloride) and oleyldimethylbenzylammonium chloride (olealkonium chloride) have the identical number of carbon atoms (18) in the long alkyl chain portion of the compound. The long alkyl chain of the oleyl compound has one degree of unsaturation with a carbon-carbon double bond at carbon atom number nine ($\Delta^9$). The long alkyl chain of thesstearyl compound is fully saturated. However, the olealkonium chloride is water soluble, whereas the stearalkonium chloride is oil soluble. Therefore, the degree of unsaturation of the along alkyl chain of the quaternary ammonium compound can effectively change the solubility characteristics of the compound. Consequently, greater water solubility is expected from a linoleic fatty acid ($\Delta^{9,12}$) derived quaternary ammonium compound and still greater water solubility is expected from a linolenic fatty acid derived quaternary ammonium compound ($\Delta^{9, 12, 15}$) compared to the water solubility properties of an oleyl fatty acid ($\Delta^9$) derived quaternary ammonium compound.

The oil-soluble, water-dispersible conditioning agents having a quaternary nitrogen atom and one or two long alkyl chains including from about 14 to about 22 carbon atoms per alkyl chain include a broad range of compounds. However, the oil-soluble conditioning agents can be broadly divided into groups based upon the structure of the substituents on the quaternary nitrogen atom, i.e., (a) compounds having one or two long carbon chains and two or three identical or different short chain alkyl groups, i.e., methyl or ethyl groups; (b) compounds having one or two long carbon chains, one benzyl group and one or two identical or different short chain alkyl groups; and (c) compounds having one long chain alkyl, one heterocyclic nitrogen-containing moiety, like morpholine or pyridine, and none or one short chain alkyl group.

In accordance with an important feature of the present invention, an oil-soluble, water-dispersible quaternary ammonium compound is hereby further defined as a compound that when mixed with a non-polar solvent, like a hydrocarbon, forms a true solution, such that the compound, when present up to its saturation point, will not separate from the oil phase; and that, when mixed with water, is dispersed when stirred or agitated, but separates from the water phase when stirring or agitation is stopped. Therefore, the following list of oil-soluble quaternary ammonium compounds are exemplary, but not limiting, of oil-soluble, water-dispersible quaternary ammonium compounds that can be used in the method and composition of the present invention:

| | |
|---|---|
| Cetyldimethylethylammonium bromide | (Cetethyldimonium bromide); |
| Cetyltrimethylammonium p-toluenesulfonate | (Cetrimonium tosylate); |
| Stearyldimethylbenzylammonium chloride | (Stearalkonium chloride); |
| Distearyldimethylammonium chloride | (Distearyldimonium chloride); |
| Dimethyldi(hydrogenated tallow)ammonium chloride | (Quaternium-18); |
| Cetyltrimethylammonium bromide | (Cetrimonium bromide); |
| Cetylethylmorpholinium ethosulfate | (Cetethylmorpholinium ethosulfate); |
| Behenyldimethylbenzylammonium chloride | (Behenalkonium chloride); |
| Behenyltrimethylammonium chloride | (Behentrimonium chloride); |
| Myristyltrimethylammonium bromide | (Mytrimonium bromide); | wherein the name in parenthesis is the compound name given in the *CTFA Dictionary*.

It should be noted that a long alkyl chain of the oil-soluble quaternary ammonium compound does not have to be solely, or primarily, of one chain length, i.e., the long chain need not be only stearyl ($C_{18}$) or behenyl ($C_{22}$). Rather, oil-soluble quaternary ammonium compounds wherein the long alkyl chain is a mixture of lengths can be used, as long as the quaternary ammonium compound is oil soluble and water dispersible. Such conditioning agents are prepared conveniently from naturally occurring materials, such as tallow, coconut oil, soya oil and the like, or from synthetically produced mixtures. Examples of conditioning agents having mixed carbon chain lengths include dimethyldi(hydrogenated tallow)ammonium chloride (Quaternium 18).

In accordance with another important feature of the present invention, the hair conditioner composition includes both a water-soluble quaternary ammonium compound, in an amount of at least about 0.35% to about 5% by weight of the composition and an oil-soluble, water-dispersible quaternary ammonium, in an amount ranging from about 0.4% to about 15% by weight of the composition; and, to achieve the full advantage of the present invention, in a ratio of water-soluble quaternary ammonium compound to oil-soluble quaternary ammonium compound ranging from about 0.1 to 1 to about 0.6 to 1, and preferably in a ratio of about 0.25 to 1 to about 0.45 to 1. As will be discussed more fully hereinafter, the combination of a water-soluble quaternary ammonium compound and an oil-soluble quaternary ammonium compound provides a hair-conditioning composition that imparts unexpectedly improved conditioning properties to hair compared to a composition that includes only either a water-soluble quaternary ammonium compound or an oil-soluble, water-dispersible quaternary ammonium compound.

The composition of the present invention also includes from about 0.1% to about 2%, and preferably from about 0.2% to about 1%, by weight of a low molecular weight polydimethylsiloxane compound. The low molecular weight polydimethylsiloxane compound is added to the composition of the present invention in an amount sufficient to provide improved combing and improved feel of the treated hair. The low molecular weight polydimethylsiloxane compound can be a linear or a cyclic polydimethylsiloxane compound as long as the polydimethylsiloxane compound provides sufficient lubrication and imparts hair conditioning properties to wet hair, and has sufficient volatility to slowly volatilize from the hair such that a residual buildup of silicone is not present on dry hair.

An example of a linear, low molecular weight, volatile polydimethylsiloxane compound useful in the composition and method of the present invention is tee compound named in the *CTFA Dictionary* as hexamethyldisiloxane, available commercially under the tradename DOW CORNING 200 FLUID, from Dow Corning Corp., Midland, Mich. Hexamethyldisiloxane has a viscosity of 0.65 cs (centistokes), is highly volatile, is non-greasy, provides lubrication, and improves the overall combing properties of the hair. Other linear polydimethylsiloxanes, such as decamethyltetrasiloxane, having a boiling point of about 195° C. and a viscosity of 1.5 centistokes; octamethyltrisiloxane; and dodecamethylpentasiloxane, also have sufficient volatility to be used in the composition of the present invention, and are preferred over hexamethyldisiloxane due to a lower volatility than hexamethyldisiloxane. In general, it has been found that linear, low molecular weight, volatile polydimethylsiloxane compounds having a viscosity at 25° C. in the range of from about 0.5 cs to about 5 cs, and a boiling point at atmospheric pressure ranging from about 100° C. to about 250° C., are suitable for use in the hair-treating composition of the present invention.

In addition, the cyclic, low molecular weight, volatile polydimethylsiloxanes, named in the *CTFA Dictionary* as cyclomethicones, can be used in the composition and method of the present invention. The cyclomethicones used in the present invention are low molecular weight, water-insoluble cyclic compounds having an average of about 3 to about 6—[O—Si(CH$_3$)$_2$]-repeating group units per molecule and boil at atomspheric pressure in a range of from about 150° C. to about 250° C. The polydimethyl cyclosiloxanes having an average of about 4 to about 5 repeating units per molecule, i.e., the tetramer and pentamer, are preferred. To achieve the full advantage of the present invention, polydimethyl cyclosiloxanes having boiling points at atmospheric pressure in the range of 170° C. to 220° C., and viscosities at 25° C. of from about 2 to about 6 centistokes are included in the composition. Suitable cyclomethicones are available commercially under the tradenames SILICONE SF-1173 (octamethylcyclotetrasiloxane) and SILICONE SF-1202 (decamethylcyclopentasiloxane) from General Electric, Waterford, New York, and SILICONE 334 FLUID and SILICONE 345 FLUID from Dow Corning Corporation, Midland, Mich., the tetramer being listed first in each instance The above-described linear and cyclic volatile silicones have been used in hair-treating compositions and in various other cosmetic compositions, such as antiperspirants, deodorants, hair sprays, hair coloring products, hair grooming products, powder and color products and stick products because their low viscosity and low surface tension provide a light, silky feel on hair and skin. However, it is both new and unexpected for a volatile polydimethylsiloxane as described above, to be combined with a water-soluble quaternary ammonium compound and an oil-soluble, water-dispersible quaternary ammonium compound, and with an acid-neutralized amidoamine compound of general structural formula (I) or (II), to provide a hair-conditioning composition that imparts such improved we stage properties, dry stage properties, rinsing properties, and overall conditioning benefits to the hair, such as a reduction of split ends, body and manageability.

In addition to the water-soluble quaternary ammonium compound, the oil-soluble quaternary ammonium compound and the low molecular weight polydimethylsiloxane compound, the composition of the present invention also includes from about 0.1% to about 5%, and preferably from about 0.1% to about 2%, by weight of an acid-neutralized amidoamine compound. In accordance with an important feature of the present invention, an amidoamine compound having the general structural formula (I) or (II):

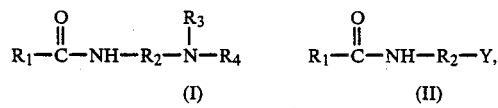

wherein $R_1$ is a fatty acid chain containing from about 11 to about 21 carbon atoms, $R_2$ is an alkylene group containing from two to about four carbon atoms, $R_3$ is hydrogen, methyl, ethyl or a hydroxyalkylene group containing from one to about three carbon atoms, $R_4$ is methyl, ethyl or a hydroxyalkylene group containing from one to about three carbon atoms, and Y is a heterocyclic nitrogen-containing moiety, like morpholine, is neutralized with a suitable acid and included in a composition to impart improved physical and cosmetic properties to hair.

An example of an amidoamine compound having the general structural formula (I) that can be used in the composition and method of the present invention is the compound named in the *CTFA Dictionary* as stearamidoethylethanolamine, available commercially under the tradename CHEMICAL BASE 39 from Sandoz, Inc., East Hanover, N.J. and having the structural formula (IV):

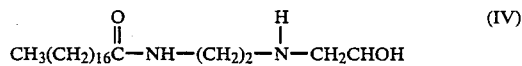

Other suitable amidoamine compounds include, but are not limited to, compounds designated in the *CTFA Dictionary* as stearamidoethyldiethanolamine, isostearamidopropylmorpholine and stearamidopropylmorpholine, having structural formulas (V), (VI) and (VII) respectively. In addition, suitable

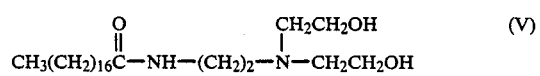

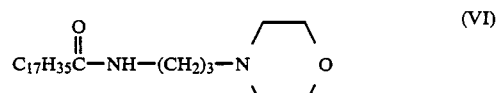

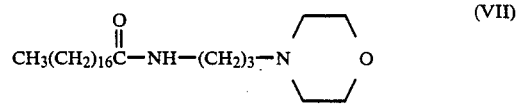

amidoamine compounds include compounds having either one or two hydroxymethyl, hydroxypropyl, methyl or ethyl moieties, or combinations thereof, present on an amino nitrogen in place of the hydroxyethyl moieties. Examples of such amidoamine compounds include, but are not limited to, dimethylaminopropyl stearamide, diethylaminoethyl stearamide, and dimethylaminopropyl myristamide. However, to achieve the full advantage of the present invention, the amidoamine compound either includes an amine nitrogen having two hydroxyalkylene moieties as substituents, or one hydrogen atom and one hydroxyalkylene moiety as substituents; or includes one heterocyclic nitrogen-containing hydroxyalkylene-type moiety, like morpholine, as the substituent.

The fatty acid chain $R_1$ of compounds of general structural formulas (I) and (II) does not have to be solely, or primarily, of one chain length, i.e., the long chain need not be derived only from lauryl ($C_{12}$), myristyl ($C_{14}$), cetyl ($C_{16}$), or stearyl ($C_{18}$). Rather, amidoamine compounds of general structural formulas (I) and (II) wherein the long alkyl chain is a mixture of lengths can be used, as long as the free amidoamine is oil soluble and water dispersible. Such amidoamine compounds are prepared conveniently from naturally-occurring materials, such as tallow, coconut oil, soya oil and the like, or from synthetically produced mixtures.

In accordance with an important feature of the present invention, after neutralization with a suitable acid, the above-described amidoamine compounds of general structural formulas (I) and (II) exhibit the properties of a cationic surfactant. In the free amine state, as depicted in general structural formulas (I) and (II) and in structural formulas (IV) through (VII), the amidoamine compounds are insoluble in water. However, after acid neutralization, the amidoamine compounds are water dispersible or water soluble. Consequently, in the acid neutralized state, the acid-neutralized amidoamine compound behaves like a cationic surfactant, and therefore is substantive to the hair and imparts conditioning properties to the hair.

The acid used to neutralize the amidoamine compound can be essentially any organic acid or mineral acid of sufficient acid strength to neutralize a free amine nitrogen. Such acids include, but are not limited to, hydrochloric acid, sulfuric acid, nitric acid, phosphoric acid, lactic acid, citric acid, tartaric acid, acetic acid, gluconic acid, glycolic acid and propionic acid, or combinations thereof. To achieve the full advantage of the present invention, the amidoamine compound is neutralized with phosphoric acid. In general, a sufficient amount of acid is added to neutralize the amidoamine compound and to adjust the final pH of the hair-treating composition to within a range of from about 4 to about 7, and more preferably in a pH range of from about 5.5 to about 6.5.

Acid-neutralized amidoamine compounds useful in the method and composition of the present invention include, but are not limited to, stearamidoethylethanolamine phosphate, obtained from stearamidoethylethanolamine (IV) neutralized with phosphoric acid; stearamidoethylethanolamine acetate, from stearamidoethylethanolamine (IV) neutralized with acetic acid; isostearamidopropylmorpholine lactate, from isostearamidopropylmorpholine (VI) neutralized with lactic acid; and stearamidopropylmorpholine lactate, from stearamidopropylmorpholine (VII) neutralized with lactic acid. Generally, the amidoamine compounds are neutralized by adding the amidoamine compound to the oil phase of an emulsion and the neutralizing acid to the water phase of the emulsion. Mixing of the phases results in neutralization of the amidoamine compound.

In addition to the four above-described essential ingredients, other common cosmetic components and additives that can be incorporated with the essential ingredients of the present invention, as long as the basic properties of the hair-treating composition are not adversely affected, include, but are not limited to, fragrances, dyes, hair colorants, opacifiers, pearlescing agents, dandruff control agents, hydrotropes, foam stabilizers, solubilizers, preservatives, water softening agents, acids, bases, buffers and the like. These optional components and additives usually will be present in weight percentages of less than about 2% each, and from about 5% to about 10% by weight in total.

The vehicle of the hair-treating composition is generally predominantly water, but organic solvents also can be used in order to help solubilize compounds that are not sufficiently soluble in water. Suitable solvents include the lower alcohols like ethyl alcohol and isopropyl alcohol; polyols like glycerol; glycols or glycol ethers, like 2-butoxyethanol, ethylene glycol, ethylene glycol monoethyl ether, propylene glycol and diethylene glycol monoethyl ether or monomethyl ether; and mixtures thereof These non-aqueous solvents can be present in the hair-treating composition of the present invention in an amount from about 1 to about 100% by weight and in particular from about 5 to about 50% by weight, relative to the total weight of the carrier vehicle in the composition.

Long chain fatty alcohols having from about 10 to about 18 carbon atoms in the alkyl chain also can be included, optionally, in a hair-treating composition of the present invention. The fatty alcohols are included in the hair-treating composition to enhance consumer appeal, to provide thickening and to assist the long term stability of the composition. As will be demonstrated more fully hereinafter, compositions of the present invention, either including or excluding the long chain fatty alcohol, demonstrate an essentially identical ability to impart hair conditioning properties to the hair. When included in a hair-treating composition of the present invention, the fatty alcohol is present in a range of from about 0.5% to about 10% by weight of the hair-treating composition, and preferably in a range of from about 1% to about 5% by weight of the composition.

The optional fatty alcohols can be used alone, or in admixture with each other. Suitable long chain fatty alcohols include, but are not limited to, lauryl alcohol, oleyl alcohol, cetyl alcohol, myristyl alcohol, stearyl alcohol, and the like; and mixtures thereof. In addition, mixtures of natural or synthetic fatty alcohols having fatty chain lengths of from about 10 to about 18 carbons also are useful. Several such mixtures are available commercially, and are exemplified by the material containing a mixture of synthetic alcohols with from 12 to 15 carbons in the alkyl chain sold under the designation NEODOL 25 by Shell Chemical Company, Houston, Tex. Furthermore, fatty alcohols of twelve to eighteen carbon chain lengths that are ethoxylated or propoxylated can be used in place of the fatty alcohols themselves. Examples of such useful ethoxylated fatty acids include ethylene glycol cetyl ether, polyoxyethylene(2)stearyl ether, polyoxyethylene(24) cetyl ether, and the like; the exemplary compounds have CFTA Dictionary names of Ceteth-1, Steareth-2 and Cetoleth-24, respectively.

The hair-treating compositions of the present invention also can be thickened, for example, with sodium alginate; guar gum; xanthan gum; gum arabic; cellulose derivatives such as methylcellulose, hydroxyethylcellulose, hydroxypropylmethylcellulose and carboxymethylcellulose; and various polymeric thickeners, such as polyacrylic acid derivatives. These thickeners are present in an amount ranging from about 0.1% to about 3%, and preferably from about 0.25% to about 1%, by weight relative to the total weight of the composition.

The hair-treating compositions also can include non-ionic surfactants to impart emulsifying properties to the composition. Likewise, the compositions can include other emulsifiers, inorganic salts, humectants and similar materials to provide esthetic properties and desirable physical properties to the composition. Generally, such optional ingredients are present in weight percentages ranging from about 0.1% to about 10% each, and from about 0.1% to about 0% in total, relative to the total weight of the composition.

For example, representative non-ionic surfactants that can be included in the hair-treating composition of the present invention include esters of polyols and sugars; the polyethoxylated and/or polypropoxylated alkylphenols; and the condensation products of ethylene oxide with long chain amides. All these non-ionic surfactants, as well as numerous others not cited here, are well known in the art and are fully described in the literature.

The compositions of the present invention can be milky-white, relatively viscous dispersions that are stable to phase separation at a temperature of about 20° C. to about 25° C. for a period of time of at least 24 hours after preparation, and typically are stable to phase separation indefinitely at such temperatures. The compositions of the present invention usually are emulsions that are stable to phase separation at a temperature of about 25° C. for a period of about 24 hours after preparation. The emulsions have demonstrated sufficient stability to phase separation at temperatures normally found in commercial product storage and shipping to remain unaffected for periods of one year or more. Upon a judicious selection of a liquid vehicle, it also is envisioned that a composition of the present invention can be a true solution.

In accordance with the method of the present invention, several hair-treating compositions were prepared, then applied to human hair, to demonstrate the improved hair conditioning properties afforded by compositions comprising a water-soluble quaternary ammonium compound; an oil-soluble, water-dispersible quaternary ammonium compound; a low molecular weight polydimethylsiloxane compound; and an acid-neutralized amidoamine compound of general structural formula (I) or (II). It has been demonstrated that, to maximize hair conditioning properties, the hair-treating composition of the present invention should include both a water-soluble quaternary ammonium compound and an oil-soluble, water-dispersible quaternary ammonium compound. Although the mechanism of interaction between these ingredients is not known, it has been theorized that the water-soluble quaternary ammonium compound acts to swell the hair fibers and separate hair cuticles. Consequently, the oil-soluble quaternary ammonium compound can more effectively contact the hair and therefore deposit on the hair in greater amounts. Furthermore, as will be demonstrated hereinafter, laboratory and salon testing has shown that optimum conditioning properties are imparted to the hair when both a water-soluble and an oil-soluble quaternary ammonium compound are present in the composition in sufficient quantity and, preferably, in the proper relative ratios.

For example, it has been found that at least about 0.35% by weight of a water-soluble quaternary ammonium compound should be present in the hair-treating compositions of the present invention. As will be discussed more fully hereinafter, it has been demonstrated that hair conditioning performance of the hair-treating composition is less pronounced when the amount of water-soluble quaternary ammonium compound in the hair-treating composition is less than about 0.35% by weight of the composition. It also has been found that an amount of water-soluble quaternary ammonium compound in the composition above about 0.35% by weight further improves performance of the hair-conditioning composition up to a level of about 5% by weight of the water-soluble quaternary ammonium compound. It further has been found that a level of water-soluble quaternary ammonium compound in the composition above about 5% by weight, such as up to about 15% by weight, does not adversely affect composition performance, but also does not appreciably improve the performance of the hair-conditioning composition. Therefore, any amounts of water-soluble quaternary ammonium compound in the composition above about 5% by weight are apparently wasted because the excess water-soluble quaternary ammonium compound is rinsed from the hair during the rinsing step of the hair treatment.

To determine the minimum amount of water-soluble quaternary ammonium compound needed to provide a composition that imparts unexpectedly improved hair conditioning properties to hair, the following compositions (Examples 1–9) first were prepared. The method of manufacture of Examples 1 through 9 is identical to the method of manufacturing the remaining Examples 10 through 37 and is described fully hereinafter. The compositions of Examples 1 through 9 then were tested for their ability to condition hair. The particular water-soluble quaternary ammonium compound used in Examples 1 through 9 was cetrimonium chloride, available under the tradename BARQUAT CT-429, from Lonza, Inc., Fair Lawn, N.J. and including 29% by weight of cetrimonium chloride; the oil-soluble quaternary ammonium compound used was distearyldimonium chloride, available under the tradename AROSURF TA-100, from Sherex Chemical Co., Dublin, 0. and including 95% by weight of distearyldimonium chloride; and the low molecular weight polydimethylsiloxane compound used was cyclomethicone, available under the tradename SILICONE SF1173 from G.E. Silicones, Waterford, N.Y. on a 100% by weight active ingredient basis. It should be understood that the following Examples 1 through 9 do not include the acid-neutralized amidoamine compound that is an essential ingredient in the hair-treating compositions of the present invention. Examples 1 through 9 were prepared and tested to help establish the limits of water-soluble and oil-soluble quaternary ammonium compounds that can be present in the hair-treating compositions of the present invention.

| INGREDIENT (% by weight) | EX. 1 | EX. 2 | EX. 3 | EX. 4 | EX. 5 | EX. 6 | EX. 7 | EX. 8 | EX. 9 |
|---|---|---|---|---|---|---|---|---|---|
| Soft Water | 95.02 | 94.82 | 94.62 | 94.42 | 94.22 | 94.02 | 93.82 | 93.62 | 93.42 |
| Thickener[1] | 0.30 | 0.30 | 0.30 | 0.30 | 0.30 | 0.30 | 0.30 | 0.30 | 0.30 |
| BARQUAT CT-429 (29% by wt. active) | 0.80 | 1.00 | 1.20 | 1.40 | 1.60 | 1.80 | 2.00 | 2.20 | 2.40 |
| AROSURF TA-100 (95% by wt. active) | 1.10 | 1.10 | 1.10 | 1.10 | 1.10 | 1.10 | 1.10 | 1.10 | 1.10 |
| Cetyl/Stearyl Alcohol | 1.90 | 1.90 | 1.90 | 1.90 | 1.90 | 1.90 | 1.90 | 1.90 | 1.90 |
| Potassium Chloride | 0.30 | 0.30 | 0.30 | 0.30 | 0.30 | 0.30 | 0.30 | 0.30 | 0.30 |
| Preservative[2] | 0.05 | 0.05 | 0.05 | 0.05 | 0.05 | 0.05 | 0.05 | 0.05 | 0.05 |
| Preservative[3] | 0.10 | 0.10 | 0.10 | 0.10 | 0.10 | 0.10 | 0.10 | 0.10 | 0.10 |
| Fragrance | 0.20 | 0.20 | 0.20 | 0.20 | 0.20 | 0.20 | 0.20 | 0.20 | 0.20 |
| Citric Acid (50% by wt. active) | 0.03 | 0.03 | 0.03 | 0.03 | 0.03 | 0.03 | 0.03 | 0.03 | 0.03 |
| SILICONE SF1173 | 0.20 | 0.20 | 0.20 | 0.20 | 0.20 | 0.20 | 0.20 | 0.20 | 0.20 |

[1] NATROSOL 250 HHR, Hercules Inc., Wilmington, DE - hydroxyethylcellulose.
[2] KATHON CG, Rohm and Haas Co., Philadelphia, PA.
[3] Glutaraldehyde CR.

It was found that Examples 1 and 2, each containing less than about 0.35% by weight of the water-soluble quaternary ammonium compound, had an initial viscosity sufficiently low such that consumer appeal would be adversely affected. Examples 3 through 9 each had a sufficient initial viscosity, i.e., 2000–7000 cps (centipoises) at 80° F. with LV4 spindle at 20 rpm and 15,000–70,000 cps at 80° F. with TA spindle at 0.5 rpm, for acceptable consumer appeal.

Furthermore, a salon evaluation comparing a composition including about 0.30% by weight water-soluble quaternary ammonium compound (EX. 2) to a composition including about 0.35% by weight of a water-soluble quaternary ammonium compound (EX. 3) was performed to determine the effect of reducing the amount of water-soluble quaternary ammonium compound below about 0.35% by weight on the ability of the composition to condition the hair. In the salon test, the composition of Example 2 was applied to the hair on the left side of the head of six test individuals and the composition of Example 3 was applied to the hair on the right side of the hair of the same test individuals. After rinsing, a test panel of five trained judges subjectively judged the condition of the hair on each side of the test individual's head on a scale of one unit to five units. In the subjective salon tests, the judges' ratings for each side of hair were averaged, and a relative difference of 0.3 units in judging the condition of one side of hair compared to the other side of hair was considered significant.

Using this criteria, it was found that the composition including about 0.35% by weight of the water-soluble quaternary ammonium compound (EX. 3) significantly outperformed the composition including about 0.30% by weight of the water-soluble quaternary ammonium compound (EX. 2) in the areas of wet feel, wet combing, manageability, condition of the ends, sheen and luster, body and the overall condition of the hair. It should be noted that among the numerous hair conditioning properties, the above-listed properties are considered the key properties in regard to hair conditioning.

Consequently, it was found that including at least about 0.35% by weight of a water-soluble quaternary ammonium compound, together with an oil-soluble quaternary ammonium compound, in a hair-treating composition of the present invention imparts unexpectedly improved hair conditioning properties to treated hair. Such a result is surprising because a water-soluble quaternary ammonium compound usually is present in a hair conditioner composition in much higher amounts than 0.35% by weight, such as from about 2% by weight to about 5% by weight, in order to observe improved hair conditioning properties because the inherent water solubility of the water-soluble quaternary ammonium compound results in much of the water-soluble quaternary ammonium compound being removed from the hair during the rinsing step.

In addition, it should be understood that weight percentages of the water-soluble quaternary ammonium compound above about 0.35% by weight also provide a composition that imparts exceptional conditioning properties to treated hair. However, above a level of about 5% by weight of the composition further appreciable improvement in hair conditioning properties is not demonstrated because the excess amount of water-soluble quaternary ammonium compound is not substantive to the hair and is removed during rinsing. In addition, such increased amounts of the water-soluble quaternary ammonium compound in the hair-treating compositions do not adversely affect the efficacy of the hair-treating composition. Therefore, the upper limit on the amount of water-soluble quaternary ammonium compound in the composition is restricted only by considerations of economics, composition stability and consumer appeal Consequently, it was discovered that the water-soluble quaternary ammonium compound can be present in the composition up to about 15% by weight of the composition, with improved hair conditioning properties observed up to a level of about 5% by weight of the composition.

Similarly, it was found that the amount of oil-soluble, water-dispersible quaternary ammonium compound in the composition can range from about 0.4% by weight of the composition to about 15% by weight of the composition. Below about 0.4% by weight, the oil-soluble quaternary ammonium compound was not present in a sufficient amount to effectively impart desirable hair conditioning properties to the hair. However, it was found that from about 0.4% to about 15% by weight, and especially from about 0.4% to about 7% by weight, the oil-soluble quaternary ammonium compound significantly improved the hair conditioning properties of hair treated with a composition of the present invention. Above about 15% by weight of the oil-soluble quaternary ammonium compound, the compositions of the present invention demonstrated a decrease in composition stability and a decrease in overall consumer appeal.

To demonstrate that a composition including a combination of a water-soluble quaternary ammonium compound and a water-insoluble quaternary ammonium compound more effectively imparts hair-conditioning properties to treated hair, the compositions of Example 10 through 15 also were prepared. The ingredients used in Examples 10 through 15 are identical to the ingredients used in Examples 1 through 9, except the that the compositions of Examples 10 through 15 also include the acid-neutralized amidoamine compound stearamidoethylethanolamine phosphate, available under the tradename SANDOTEX A from Sandoz, Inc., East Hanover, N.J., and including about 23% by weight of stearamidoethylethanolamine phosphate.

| INGREDIENT (% by weight) | EX. 10 | EX. 11 | EX. 12 | EX. 13 | EX. 14 | EX. 15 |
|---|---|---|---|---|---|---|
| Soft Water | 93.99 | 91.68 | 94.79 | 94.39 | 95.89 | 94.79 |
| Thickener[1] | 0.30 | 0.30 | 0.30 | 0.30 | 0.30 | 0.30 |
| BARQUAT CT-429 (29% by wt. active) | 1.20 | 4.61 | — | 1.00 | 1.20 | 1.20 |
| AROSURF TA-100 (95% by wt. active) | 1.10 | — | 1.50 | 0.90 | 1.10 | 1.10 |
| SANDOTEX A (23% by wt. active) | 0.60 | 0.60 | 0.60 | 0.60 | 0.60 | — |
| Cetyl/Stearyl Alcohol | 1.90 | 1.90 | 1.90 | 1.90 | — | 1.90 |
| Potassium Chloride | 0.30 | 0.30 | 0.30 | 0.30 | 0.30 | 0.30 |
| Preservative[2] | 0.08 | 0.08 | 0.08 | 0.08 | 0.08 | 0.08 |
| Preservative[3] | 0.10 | 0.10 | 0.10 | 0.10 | 0.10 | 0.10 |
| Fragrance | 0.20 | 0.20 | 0.20 | 0.20 | 0.20 | 0.20 |
| Citric Acid (50% by wt. active) | 0.03 | 0.03 | 0.03 | 0.03 | 0.03 | 0.03 |
| SILICONE SF1173 | 0.20 | 0.20 | 0.20 | 0.20 | 0.20 | — |

[1] NATROSOL 250 HHR, Hercules, Inc., Wilmington, DE - hydroxyethylcellulose.
[2] KATHON CG, Rohm and Haas Co., Philadelphia, PA.
[3] Glutaraldehyde CR.

The composition of Example 10 is a composition of the present invention including each of the four essential ingredients, namely a water-soluble quaternary ammonium compound, an oil-soluble quaternary ammonium compound, an acid-neutralized amidoamine compound, and a low molecular weight (polydimethylsiloxane compound. Example 11 is a hair conditioning composition similar to the composition of Example 10, except the oil-soluble quaternary ammonium compound is omitted from the composition. Similarly, Example 12 is a hair conditioning compound similar to Example 10, but the water-soluble quaternary ammonium compound is omitted from the composition. However, Examples 10 through 12 each include a total amount of quaternary ammonium compounds in the range of from about 1.35% to about 1.40% by weight. Example 13 is a composition of the present invention identical to Example 10, but including only about 1.15% by weight total amount of quaternary ammonium compounds compared to about 1.40% by weight total amount of quaternary ammonium compounds in Example 10. Example 14 is a composition of the present invention absent the optional fatty alcohols. Example 15 is a prototype formulation of a commercially-available hair conditioner, i.e., SUAVE, available from Helene Curtis, Inc., Chicago, Ill., that includes both a water-soluble quaternary ammonium compound and an oil-soluble quaternary ammonium compound, but does not include either an acid-neutralized amidoamine compound or a low molecular weight polydimethylsiloxane compound.

A salon evaluation comparing a composition of the present invention (EX. 10) to a substantially similar composition that omits the oil-soluble quaternary ammonium compound (EX. 11) was performed to determine the effect of eliminating an oil-soluble quaternary ammonium compound from the composition of the present invention. This salon evaluation was performed in an identical manner to the previously-described salon evaluation, with a relative difference of 0.3 units in the subjective judging being considered as significant. Accordingly, it was found that a composition of the present invention (EX. 10) significantly outperformed a hair conditioning composition absent an oil-soluble quaternary ammonium compound (EX. 11) in the area of static control Conversely, the composition of Example 11 significantly outperformed the composition of Example 10 in the areas of wet combing sheen/luster, and body. These results can be explained by the presence of a low molecular weight polydimethylsiloxane compound and the absence of the oil-soluble quaternary ammonium compound in Example 11. Accordingly, the polydimethylsiloxane compound was not competing with the highly-substantive oil-soluble quaternary ammonium compound and substantially more sites on the hair were available for deposition by the cyclomethicone than are available where an oil-soluble quaternary ammonium compound is included in the composition (i.e., EX. 10). The increased cyclomethicone deposition provides increased sheen/luster, as well as wet combing benefits. However, these benefits are short-lived and diminish relatively quickly as the cyclomethicone evaporates from the hair shaft. In general, the composition of Example 11 is considered an ineffective hair conditioner because of the above-described disadvantages and because the composition did not provide an effective control of static electricity, a fundamental requirement of any useful hair conditioning composition.

Similarly, the composition of Example 10 was compared to the composition of Example 12 in another salon evaluation. The composition of Example 12 is similar to the composition of Example 10, but a water-soluble quaternary ammonium compound is omitted in the composition of Example 12. Accordingly, it was found that a composition of the present invention (EX. 10) significantly outperformed a hair conditioning composition absent a water-soluble quaternary ammonium compound (EX. 12) in the areas of ease of application, wet feel, wet combing, dry combing, dry feel, condition of ends and overall condition. It also should be noted that for wet feel and wet combing, the composition of Example 10 outperformed Example 12 by 0.8 and 0.7 rating units. This large difference in subjective rating units is considered a very significant performance difference in a salon evaluation.

Overall, the two above-described salon evaluations demonstrate that a hair conditioner composition of the present invention, including both a water-soluble quaternary ammonium compound and an oil-soluble quaternary ammonium compound significantly outperform a hair conditioning composition including only either a water-soluble quaternary ammonium compound or an oil-soluble quaternary ammonium compound Compositions including both a water-soluble quaternary ammonium compound and an oil-soluble quaternary ammonium compound have been used to condition hair, as shown in the prototype formula for SUAVE in Example 15. However, such compositions have not further included an acid-neutralized amidoamine or a low molecular weight polydimethylsiloxane compound to unexpectedly further improve the hair conditioning properties imparted to the hair.

In order to demonstrate the new and unexpected benefits achieved by a composition of the present invention, a composition of the present invention (EX. 13) was compared to the SUAVE formulation (EX. 15). The composition of Example 13 includes about 20% less active quaternary ammonium compound than the composition of Example 15. In Example 15, the acid-neutralized amidoamine compound and the low molecular weight polydimethylsiloxane compound are omitted. Surprisingly, in a salon evaluation, the composition of Example 13, including a reduced amount of quaternary ammonium compounds, essentially equalled the performance of Example 15 in imparting hair conditioning properties to hair, and actually significantly outperformed Example 15 in the areas of dry combing and dry feel. Another composition of the present invention (EX. 14), that omitted the optional fatty alcohol from the composition, also was compared to the SUAVE prototype formulation (EX. 15) in a salon evaluation. The salon evaluation showed no significant differences between the ability of Example 14 and Example 15 to impart hair conditioning properties to hair, thereby indicating that the fatty alcohol is an optional as opposed to an essential, ingredient in the composition of the present invention.

In general, the above-described salon evaluations comparing the compositions of Examples 10 through 15, show that each of the four essential ingredients of the present invention are necessary to provide a composition that imparts such superior and improved hair conditioning properties to hair. The above salon evaluations demonstrate that not only is a combination of a water-soluble quaternary ammonium compound and an oil-soluble quaternary ammonium compound essential to the method and composition of the present invention, but the composition also must include an acid-neutralized amidoamine and a low molecular weight polydimethylsiloxane compound.

In addition, although the oil-soluble quaternary ammonium compound can be present in the hair-treating composition in an amount ranging from about 0.4% by weight to about 15% by weight, to achieve the full advantage of the present invention, the amount of oil-soluble quaternary ammonium compound in the composition is balanced with the amount of water-soluble quaternary ammonium compound in the composition in order to provide a composition that imparts superior conditioning properties to the hair. Consequently, it has been found that the ratio of water-soluble quaternary ammonium compound to oil-soluble quaternary ammonium compound in the hair-treating composition in the range of from about 0.1 to 1 to about 0.6 to 1, and more preferably, in the range of from about 0.25 to 1 to about 0.45 to 1, provides a composition that imparts superior conditioning properties to hair. Within these limits, a sufficient amount of water-soluble quaternary ammonium compound is present to swell the hair fibers and a sufficient amount of oil-soluble quaternary ammonium compound is present to deposit on the swelled hair fibers, even at the lower concentration limits for the two quaternary ammonium compound components.

Furthermore, it was found that the volatile, low molecular weight polydimethylsiloxane should be present in an amount of at least about 0.1% by weight of the composition to further improve the conditioning properties of the hair. Similarly, it was found that the amount of low molecular weight polydimethylsiloxane in the hair-treating composition can be increased up to about 2% by weight without adversely affecting the composition. However, at levels above about 2% by weight of a polydimethylsiloxane the compositions demonstrated decreased stability with respect to phase separation. To achieve the full advantage of the present invention, compositions including from about 0.1% to about 1% by weight of the low molecular weight polydimethylsiloxane demonstrated the optimum balance between composition stability and ability to impart improved hair conditioning properties.

In accordance with an important feature of the present invention, it has been found that including an acid-neutralized amidoamine compound, in an amount ranging from about 0.1% to about 5% by weight of the composition, in a hair-treating composition including a low molecular silicone, a water-soluble quaternary ammonium compound and an oil-soluble quaternary ammonium compound substantially improves the hair conditioning properties of treated hair. To achieve the full advantage of the present invention, the acid-neutralized amidoamine compound is present in a range of from about 0.2% to about 1% by weight of the composition. The amount of acid-neutralized amidoamine compound in the composition is independent of the amounts, and the ratio, of the water-soluble and the oil-soluble quaternary ammonium compounds in the composition. It should be understood that an acid-neutralized amidoamine compound of general structural formula (I) or (II) is an essential ingredient in the composition of the present invention in that the acid-neutralized amidoamine compound helps impart superior hair conditioning properties to hair treated with a composition of the present invention having a surprisingly low total amount of active hair conditioning components.

To demonstrate the effect of including an acid-neutralized amidoamine compound in a hair-treating composition of the present invention, Examples 16 through 20 were prepared. Examples 16 through 20 are similar to Examples 1 through 9 except the amount of water-soluble quaternary ammonium compound was maintained at about 1.2% by weight of BARQUAT CT-429, or at about 0.35% by weight of active water-soluble quaternary ammonium compound, and a portion of the oil-soluble quaternary ammonium compound, AROSURF TA-100, was replaced with an acid-neutralized amidoamine compound. The particular acid-neutralized amidoamine compound used in Examples 16 through 20 is stearamidoethylethanolamine acetate, available commercially under the tradename CERANINE HCA from Sandoz, Inc., East Hanover, N.J. on 100% by weight active ingredient basis.

| INGREDIENT (% by weight) | EX. 16 | EX. 17 | EX. 18 | EX. 19 | EX. 20 |
|---|---|---|---|---|---|
| Soft Water | 94.70 | 94.69 | 94.68 | 94.67 | 94.66 |
| Thickener[1] | 0.30 | 0.30 | 0.30 | 0.30 | 0.30 |
| BARQUAT CT-429 (29% by wt. active) | 1.20 | 1.20 | 1.20 | 1.20 | 1.20 |
| AROSURF TA-100 (95% by wt. active) | 0.27 | 0.38 | 0.49 | 0.60 | 0.71 |
| CERANINE HCA (100% by wt. active) | 0.75 | 0.65 | 0.55 | 0.45 | 0.35 |
| Cetyl/Stearyl Alcohol | 1.90 | 1.90 | 1.90 | 1.90 | 1.90 |
| Potassium Chloride | 0.30 | 0.30 | 0.30 | 0.30 | 0.30 |
| Preservative[2] | 0.05 | 0.05 | 0.05 | 0.05 | 0.05 |
| Preservative[3] | 0.10 | 0.10 | 0.10 | 0.10 | 0.10 |
| Fragrance | 0.20 | 0.20 | 0.20 | 0.20 | 0.20 |
| Citric Acid (50% by wt. active) | 0.03 | 0.03 | 0.03 | 0.03 | 0.03 |
| SILICONE SF1173 | 0.20 | 0.20 | 0.20 | 0.20 | 0.20 |

[1]NATROSOL 250 HHR, Hercules Inc., Wilmington, DE - hydroxyethylcellulose.
[2]KATHON CG, Rohm and Haas Co., Philadelphia, PA.
[3]Glutaraldehyde CR.

Examples 16 through 20, like Examples 1 through 15 and all remaining Examples, were manufactured by first adding the thickener to a major portion of the soft water. The thickener was thoroughly dispersed in the water by high speed stirring, and the resulting dispersion then was heated. When the dispersion reached a temperature of about 150° F., and under conditions of continuous stirring, the BARQUAT CT-429 was added. Upon continued heating, when the resulting mixture reached a temperature of about 160° F., the AROSURF TA-100 and CERANINE HCA were added slowly. The resulting mixture was maintained at 160° F. and stirred until homogeneous. The resulting homogeneous mixture then was heated to 175° F., followed by the addition of the cetyl/stearyl alcohol. The mixture was maintained at a temperature of 175° F. and stirred until homogeneous. This homogeneous mixture then was allowed to cool, and, upon attaining a temperature of about 150° F., the major portion of the remaining soft water was added to the mixture. The minor portion of the remaining soft water was used to dissolve the potassium chloride. This potassium chloride solution was added, with stirring, to the mixture after the mixture cooled to a temperature of about 120° F. After the resulting mixture further cooled to about 110° F., the KATHON CG, glutaraldehyde CG, fragrance and liquid citric acid were added to the mixture. Finally, when the mixture cooled to about 95° F., the SILICONE SF1173 was added and the resulting mixture stirred until homogeneous. After cooling to room temperature, the resulting composition was a yellowish emulsion having a pH in the range of from about 5.1 to about 5.3.

Examples 16 through 20 were subsequently tested on bleached blond tresses. In general, the compositions of Examples 16 through 20 imparted improved hair conditioning properties to the bleached blond tresses compared to bleached blond tresses treated with a conditioning composition absent the acid-neutralized amidoamine compound. It also was found that hair treated with the composition of Example 18, including about 0.55% of stearamidoethylethanolamine acetate, demonstrated the most improved hair conditioning properties.

To further show the beneficial effect of including an acid-neutralized amidoamine compound in the hair-treating composition of the present invention, Examples 21 through 25 were prepared. Examples 21 through 25 are similar to Examples 1 through 20 except the amount of water-soluble quaternary ammonium compound was maintained at about 0.35% by weight, the amount of oil-soluble quaternary ammonium compound was maintained at about 1.05% by weight, for a ratio of water-soluble quaternary ammonium compound to oil-soluble quaternary ammonium compound of 0.33 to 1, and the acid-neutralized amidoamine compound used was stearamidoethylethanolamine phosphate, available under the tradename SANDOTEX A from Sandoz, Inc., East Hanover, N.J. and including about 23% by weight of stearamidoethylethanolamine phosphate. Examples 21 through 25 include from 0.50% to 0.90% by weight of SANDOTEX A, i.e., from about 0.1% to about 0.21% by weight of stearamidoethylethanolamine phosphate. Each of Examples 21 through 25 was prepared by a method identical to the method of manufacturing Examples 16 through 20.

| INGREDIENT (% by weight) | EX. 21 | EX. 22 | EX. 23 | EX. 24 | EX. 25 |
|---|---|---|---|---|---|
| Soft Water | 94.12 | 94.02 | 93.92 | 93.82 | 93.72 |
| Thickener[1] | 0.30 | 0.30 | 0.30 | 0.30 | 0.30 |
| BARQUAT CT-429 (29% by wt. active) | 1.20 | 1.20 | 1.20 | 1.20 | 1.20 |
| AROSURF TA-100 (95% by wt. active) | 1.10 | 1.10 | 1.10 | 1.10 | 1.10 |
| SANDOTEX A (23% by wt. active) | 0.50 | 0.60 | 0.70 | 0.80 | 0.90 |
| Cetyl/Stearyl Alcohol | 1.90 | 1.90 | 1.90 | 1.90 | 1.90 |
| Potassium Chloride | 0.30 | 0.30 | 0.30 | 0.30 | 0.30 |
| Preservative[2] | 0.05 | 0.05 | 0.05 | 0.05 | 0.05 |
| Preservative[3] | 0.10 | 0.10 | 0.10 | 0.10 | 0.10 |
| Fragrance | 0.20 | 0.20 | 0.20 | 0.20 | 0.20 |
| Citric Acid (50% by wt. active) | 0.03 | 0.03 | 0.03 | 0.03 | 0.03 |
| SILICONE SF1173 | 0.20 | 0.20 | 0.20 | 0.20 | 0.20 |

[1]NATROSOL 250 HHR, Hercules Inc., Wilmington, DE - hydroxyethylcellulose.
[2]KATHON CG, Rohm and Haas Co., Philadelphia, PA.
[3]Glutaraldehyde CR.

The compositions of Examples 21 through 25 were applied to hair, then compared to each other and to a leading commercial hair conditioner, FINESSE, available from Helene Curtis, Inc., Chicago, Ill., for an ability to impart hair conditioning properties the hair. This preliminary testing demonstrated that all of the compositions of Examples 21 through 25, and especially the composition of Example 22, compared favorably to FINESSE, a conditioner including approximately three times greater an amount of active ingredients (by weight) than EXS. 21 through 25 and recognized in the art as imparting exceptional hair conditioning properties to hair.

In particular, to further demonstrate the improved hair conditioning properties imparted to hair treated with the composition of Example 22, a group of eight laboratory panelists rated hair treated with either the composition of Example 22, or the commercially-available hair conditioner FINESSE, or the commercially-available hair conditioner SUAVE (EX. 15). FINESSE includes a quaternary ammonium compound, an amidoamine compound and a polydimethylsiloxane in a total amount of about 4.4% by weight. SUAVE includes a water-soluble quaternary ammonium compound and an oil-soluble quaternary ammonium compound in approximately the same weight percentages as present in EXS. 21 through 25. SUAVE does not include an amidoamine or a polydimethylsiloxane; FINESSE does not include a blend of a water-soluble and an oil-soluble quaternary ammonium compound. Both SUAVE and FINESSE are available from Helene Curtis, Inc., with FINESSE being recognized as an exceptional hair conditioning product and SUAVE being recognized as a premium hair conditioning product.

The panelists, in a blind test, subjectively rated the treated hair with respect to wet combing as best (5), middle (3) and worst (1). After averaging the panelists' results, hair treated with FINESSE received an average rating of 4, the hair treated with SUAVE received an average rating of 1.6, and the hair treated with the composition of Example 22 received an average rating of 3. Therefore, it was observed that a composition of the present invention substantially outperformed a premium hair-conditioning product, and approaches the performance of an exceptional hair conditioning product. Such results were both surprising and unexpected because of the low amount of total active ingredients present in the composition of Example 22.

In accordance with another important feature of the present invention, compositions designated as Examples 26 and 27 were prepared, then compared to the composition of Example 22 for their ability to impart hair conditioning properties to hair. Examples 26 and 27 are identical to Example 22, except that the SANDOTEX A in Example 22 is replaced by CERANINE HCA in Example 26 and that SANDOTEX A in Example 22 is replaced by the compound of structural formula (VIII), stearamidopropyldimethylamine, commercially available from Inolex Chem., Philadelphia, Pa. under the tradename LEXAMINE S-13 in Example 27. LEXAMINE S-13 includes 100% by weight of active stearamidopropyldimethylamine. It should be noted that LEXAMINE S-13

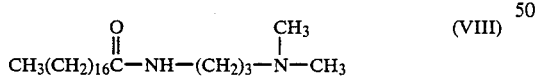

$$CH_3(CH_2)_{16}\overset{O}{\overset{\|}{C}}-NH-(CH_2)_3-\overset{CH_3}{\overset{|}{N}}-CH_3 \quad (VIII)$$

includes an amino nitrogen including alkyl, i.e., methyl, moieties as substituents, rather than the hydroxyalkyl and hydrogen moieties of SANDOTEX A and CERANINE HCA.

It also should be noted that SANDOTEX A and CERANINE HCA are commercially-available in the acid-neutralized form, whereas the LEXAMINE S-13 is commercially-available in the free amine form. Therefore, the LEXAMINE S-13 was converted to the acid-neutralized form in situ by citric acid after the LEXAMINE S-13 was thoroughly admixed into the composition. Alternatively, the LEXAMINE S-13 can be converted to the acid-neutralized form by neutralizing the LEXAMINE S-13 with citric acid before the amidoamine compound is admixed into the composition. In addition, any amidoamine having general structural formula (I) or (II) can be converted to the acid-neutralized form by either of the above-described neutralization procedures.

After applying the compositions of Examples 22, 26 and 27 to hair, a group of eight laboratory panelists rated hair treated with the composition of EX. 22 or of EX. 26, including either SANDOTEX A or CERANINE HCA, substantially superior in conditioning properties to hair treated with the composition of EX. 27 including acid-neutralized LEXAMINE S-13. It was found that on a subjective scale of 1 unit to 5 units (worst to best), the average panelist rating for hair treated with the composition of Example 22 was 4.00 and for hair treated with the composition of Example 26 was 3.25. However, hair treated with the composition of Example 27 attained an average panelist rating of only 1.75. Consequently, it has been demonstrated that compositions of the present invention including acid-neutralizing amidoamine compounds having oxygen-containing moieties on the amine nitrogen, surprisingly and unexpectedly, improve the hair conditioning properties of treated hair compared to hair treated with compositions that include an acid-neutralized amidoamine compound having alkyl moieties as substituents on the amine nitrogen.

To further shown that compositions of the present invention including acid-neutralized amidoamine compounds having oxygen-containing moieties on the amine nitrogen impart greater hair conditioning properties to hair than compositions including acid-neutralized amidoamine compounds having alkyl moieties on the amine nitrogen, the composition of Example 28 was prepared.

| INGREDIENT (% by weight) | EX. 28 |
|---|---|
| Soft Water | 94.423% |
| Thickener[1] | 0.300% |
| Phosphoric Acid (85% by wt. active) | 0.017% |
| BARQUAT CT-429 (29% by wt. active) | 1.200% |
| AROSURF TA-100 (95% by wt. active) | 1.100% |
| LEXAMINE S-13 (100% by wt. active) | 0.150% |
| Cetyl/Stearyl Alcohol | 1.900% |
| Potassium Chloride | 0.300% |
| Preservative[2] | 0.080% |
| Preservative[3] | 0.100% |
| Fragrance | 0.200% |
| Citric Acid (50% by wt. active) | 0.030% |
| SILICONE SF1173 | 0.200% |

[1]NATROSOL 250 HHR, Hercules Inc., Wilmington, DE - hydroxyethylcellulose.
[2]KATHON CG, Rohm and Haas Co., Philadelphia, PA.
[3]Glutaraldehyde CR.

The composition of Example 28 is a composition of the present invention including stearamidopropyldimethylamine phosphate as the acid-neutralized amidoamine compound. The composition of Example 28 was compared to the composition of Example 10, that includes stearamidoethylethanolamine phosphate as the acid-neutralized amidoamine compound, in a salon evaluation test. It should be noted that in both EX. 28 and 10 the amidoamine compound is neutralized with phosphoric acid, thereby eliminating any effects the neutralizing acid may have on the ability of the composition to impart hair conditioning properties to treated hair. Accordingly, in a salon evaluation, it was found that the composition of Example 10 significantly outperformed the composition of Example 28 in the areas of wet feel, wet combing, dry combing and condition of the ends. Consequently, to achieve the full advantage of the present invention, the amidoamine compound included in the composition is an amidoamine compound having an oxygen-containing moiety on the amine nitrogen.

To demonstrate the new and unexpected results achieved by treating hair with a hair conditioner composition comprising a water-soluble quaternary ammonium compound, an oil-soluble quaternary ammonium compound, a low molecular weight polydimethylsiloxane, and an acid-neutralized amidoamine compound having general structural formula (I) or (II), the following series of experiments were performed. The composition of Example 22 was used as a standard, and included a water-soluble quaternary ammonium compound at a level of about 0.35% by weight; an oil-soluble, water-dispersible quaternary ammonium compound at a level of about 1.05% by weight; a phosphoric acid-neutralized amidoamine compound, stearamidoethylethanolamine phosphate, at a level of about 0.12% by weight; and cyclomethicone a level of about 0.2% by weight, with the latter three components totaling about 1.37% active material.

As previously described, in Examples 1 through 9, the water-soluble quaternary ammonium compound should be present in an amount of at least about 0.35% by weight to achieve the advantages and benefits of the present invention. Therefore, in the following experiments, the water-soluble quaternary ammonium compound is maintained at this minimum amount of about 0.35% by weight. However, the amounts of AROSURF TA-100, SANDOTEX A and/or SILICONE SF1173 were varied in the following experiments such that the total active amount of the three ingredients was maintained at 1.37% by weight, the same combined weight of these three components present in Example 22. Consequently, the effects of eliminating at least one of these three essential components relative to the other two components could be determined.

TABLE I shows the effect of maintaining the amount of water-soluble quaternary ammonium compound in the composition at 0.35% by weight and eliminating one or two of the three other essential composition components, AROSURF TA-100, SANDOTEX A or SILICONE SF1173, while maintaining a total active ingredient amount of 1.37% of these ingredients included in the composition. TABLE I lists Example 22 and Examples 29 through 37, wherein the hair-treating composition was prepared, then applied to hair tresses. The hair tresses were normal six inch bleached blond human hair tresses, available from DeMeo Brothers, N.Y., N.Y. In separate experiments, one gram of the hair-treating compositions of Examples 22 and 29 through 37 each were applied to a clean, freshly-shampooed tress of hair. After contacting the tress of hair for about 60 seconds, the hair-treating composition was rinsed from the hair with tap water for 10 seconds. Laboratory panelists then combed through the wet, treated tresses of hair and ranked the differences when compared, side to side, with hair tresses treated in the identical manner with the commercially-available SUAVE conditioner.

TABLE I

| | PERCENT TOTAL ACTIVES OF KEY INGREDIENTS USED (by wt. %) | | | | | |
|---|---|---|---|---|---|---|
| EXAMPLE NO. | WATER-SOLUBLE QUATERNARY AMMONIUM COMPOUND | OIL-SOLUBLE QUATERNARY AMMONIUM COMPOUND | ACID-NEUTRALIZED AMIDO-AMINE COMPOUND | LOW MOLECULAR WEIGHT CYCLO-METHICONE | PERFORMANCE RATING DIFFERENCES VS. SUAVE | |
| | | | | | WET COMB | WET FEEL |
| 29 | 0.35 | 1.37 | — | — | — — | NONE |
| 30 | 0.35 | — | 1.37 | — | — — — — — | — — — — |
| 31 | 0.35 | — | — | 1.37 | +++ | NONE |
| 32 | 0.35 | 1.06 | — | 0.32 | + | ++++ |
| 33 | 0.35 | 1.17 | — | 0.20 | — — — | + |
| 34 | 0.35 | — | 1.17 | 0.20 | + | — |
| 35 | 0.35 | — | 0.12 | 1.25 | — | +++ |
| 36 | 0.35 | 1.05 | 0.32 | — | ++++++ | +++ |
| 37 | 0.35 | 1.24 | 0.12 | — | ++++ | +++++ |
| 22 | 0.35 | 1.05 | 0.12 | 0.20 | ++++ | + |

In interpreting the data of TABLE I, each "+" or "—" sign represents a one-quarter point of rated difference between the test composition and SUAVE. An entry of "NONE" means that no performance differences between SUAVE and the text Example were noted. For example, the hair treated with the composition of Example 22 demonstrated a one point of rated difference improvement in wet comb, and a one-quarter rated difference improvement in wet feel over hair treated with SUAVE conditioner. The compositions of Examples 29, 30 and 31 included, in addition to the water-soluble quaternary ammonium compound, only one of the remaining three essential components at a level of 1.37% total active ingredients by weight. The compositions of Example 32 through 37 included, in addition to the water-soluble quaternary ammonium compound, two of the remaining three remaining essential components at a combined level of 1.37% total active ingredients by weight.

A thorough examination of TABLE I reveals that Examples 29, 30 and 31, including only one of the three remaining essential ingredients, did not perform as well as Example 22, or impart hair conditioning properties superior to SUAVE. It should be understood that the SUAVE conditioner does include AROSURF TA-100 and BARQUAT CT-429, but does not include SILI- CONE SF1173 or SANDOTEX A. Examples 32 and 33, 34 and 35, and 36 and 37 each paired two of the three essential ingredients. Although it appears that the most substantial improvements in hair conditioning properties over SUAVE were demonstrated for a composition including only BARQUAT 429, AROSURF TA-100 and SANDOTEX A and absent SILICONE SF1173 (EXS. 36 and 37), it should be noted that these evaluations were conducted only on the wet conditioning attributes of wet comb and wet feel; and subsequent testing has demonstrated that SILICONE SF1173 is necessary in the compositions of the present invention to provide an overall improvement in both the wet stage and the dry stage of conditioned hair. Furthermore, the superior performance of Examples 22, 36 and 37 compared to SUAVE and Examples 29-37 demonstrates the unexpected results achieved by including a water-soluble quaternary ammonium compound; an oil-soluble quaternary ammonium compound and an acid-neutralized amidoamine of general structural formula (I) or (II) in a hair-conditioning composition. In addition, the effect of including an acid-neutralized amidoamine of general structural formula (I) or (II) is further demonstrated by comparing the performance of Example 37 to Example 29, wherein the addition of 0.12% by weight of the acid-neutralized amidoamine led to a surprising improvement in hair conditioning properties.

To further demonstrate that compositions of the present invention unexpectedly impart superior hair conditioning properties to hair, the composition of Example 22, including all four of the essential ingredients and the compositions of Examples 36 and 37, including three of the essential ingredients but absent the low molecular weight polydimethylsiloxane, were salon tested. Examples 22, 36 and 37 each were compared to commercially-available FINESSE conditioner and SUAVE conditioner for their ability to impart hair conditioning properties to treated hair. In this subjective testing, if a composition imparts hair conditioning properties to treated hair equivalent to the properties imparted by FINESSE, the composition is considered an exceptional conditioner because FINESSE is recognized as a benchmark for hair conditioning performance. Accordingly, if a composition imparts hair conditioning properties to treated hair equivalent to properties imparted by SUAVE, the composition is considered a premium conditioner because SUAVE is recognized as a superior conditioner, but not as efficacious as FINESSE.

As previously described, in a salon test the composition of interest is applied to one side of a head of hair, and the product used for comparison, i.e., either FINESSE or SUAVE, is applied to the other side of the head. After the treatment, each side of hair is judged for a variety of hair conditioning properties by a panel of five trained judges on a ranking of 1 unit (worst) to 5 units (best). Then ratings of the judges for each hair conditioning property are averaged, and a difference in rating one side of hair compared to the other side of hair of at least 0.3 units is considered a significant difference for that particular hair conditioning property. The judges rate the hair for such hair conditioning properties as ease of application, fragrance, ease of rinsing, wet feel, wet comb, residue, dry combing, dry feel, coating, flakes/dust, static manageability, condition of ends, sheen/luster, body, effect on hair color, irritation and overall condition.

Accordingly, it was found that in a salon comparative test of the composition of Example 22 and SUAVE conditioner, that a significant improvement (i.e., at least 0.3 rating units) in wet feel, wet combing, dry combing and condition of ends was found in hair treated with the composition of Example 22. Furthermore, in none of the above-listed hair conditioning properties did SUAVE outperform the composition of Example 22 to a significant degree. In addition, an identical salon comparative test was performed between the composition of Example 22 and FINESSE. In this comparative test, the composition of Example 22 and FINESSE compared essentially identically, except that FINESSE demonstrated a 0.3 unit improvement in condition of ends. For all the remaining hair conditioning properties, the ratings were identical or less than the significant difference of 0.3 rating units. Considering the exceptional hair conditioning properties imparted to hair by FINESSE( and that FINESSE includes about three times greater an amount of active ingredients (by weight) than the composition of Example 22, it is both surprising and unexpected for a composition of the present invention (EX. 22) to impart essentially the identical hair conditioning properties because the composition of Example 22 includes such a low total percentage of active ingredients, and is such a low cost composition.

The composition of Example 36, absent the low molecular weight polydimethylsiloxane, was compared to SUAVE in a salon test and found to be essentially identical to SUAVE in an ability to impart hair conditioning properties to hair. However, in a salon comparative test of the composition of Example 36 and FINESSE, the hair treated with FINESSE demonstrated significantly better dry stage properties of dry feel and body. Consequently, the low volatile polydimethylsiloxane is needed to impart improved dry stage hair conditioning properties to hair. Similarly, a salon comparative test of the composition of Example 37 and SUAVE demonstrated a slightly better than SUAVE performance for the composition of Example 37. However, the composition of Example 37 demonstrated a slightly worse performance than FINESSE in a salon comparative test. Overall, the above salon comparative tests demonstrate that compositions of the present invention, including a water-soluble quaternary ammonium compound, an oil-soluble quaternary ammonium compound, a low molecular weight polydimethylsiloxane, and an acid-neutralized amidoamine compound, surprisingly and unexpectedly have an improved ability to impart hair conditioning properties to hair.

Therefore, the method and composition of the present invention impart exceptional hair conditioning properties to treated hair usually demonstrated only by compositions including a much higher percentage of active ingredients. It is both surprising and unexpected for a composition of the present invention, including a water-soluble quaternary ammonium compound, an oil-soluble quaternary ammonium compound, a low molecular weight polydimethylsiloxane and an acid-neutralized amidoamine compound, to impart such improved hair conditioning properties when the total amount of active ingredients is present in such a small percentage.

In addition, the method of the present invention provides the further benefits of not leaving the hair tacky or sticky; not forming a crust and therefore providing combability; and providing manageable and styleable hair having body. In addition, after treating the hair with the composition of the present invention, the hair feels natural and thickened, has body, is soft, shiny, manageable, and combable. These beneficial effects can be achieved by using an aqueous or non-aqueous spray or solution formulation or emulsion formulation.

Obviously, many modifications and variations of the invention as hereinbefore set forth can be made without departing from the spirit and scope thereof and therefore only such limitations should be imposed as are indicated by the appended claims.

I claim:

1. A hair-treating composition comprising at least about 0.35% by weight of a water-soluble quaternary ammonium compound, wherein the water-soluble quaternary ammonium compound has the general structure:

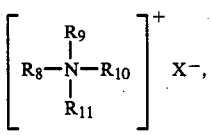

wherein $R_8$ is an alkyl group including from about 8 to about 18 carbon atoms; $R_9$ is selected from the group consisting of an alkyl group including from about 8 to about 18 carbon atoms, a hydrogen atom, a methyl group, an ethyl group, a hydroxymethyl group and a hydroxyethyl group; $R_{10}$ is selected from the group consisting of a benzyl group, a hydrogen atom, a methyl group, an ethyl group, a hydroxymethyl group and a hydroxyethyl group; $R_{11}$ is selected from the group consisting of a hydrogen atom, a methyl group, an ethyl group, a hydroxymethyl group and a hydroxyethyl group; and X is selected from the group consisting of chloride, methosulfate, ethosulfate and nitrate; from about 0.4% to about 15% by weight of an oil-soluble quaternary ammonium compound, wherein the oil-soluble quaternary ammonium compound has the general structure:

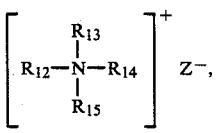

wherein $R_{12}$ is an alkyl group including from about 14 to about 22 carbon atoms; $R_{13}$ is selected from the group consisting of an alkyl group including from about 14 to about 22 carbon atoms, a methyl group and an ethyl group; $R_{14}$ is selected from the group consisting of a benzyl group, a methyl group and an ethyl group; $R_{15}$ is selected from the group consisting of a methyl group and an ethyl group; and Z is selected from the group consisting of chloride, bromide, methosulfate, ethosulfate, tosylate, acetate and phosphate; from about 0.1% to about 5% by weight of an acid-neutralized amidoamine, wherein the acid-neutralized amidoamine comprises an amidoamine compound having the general structure:

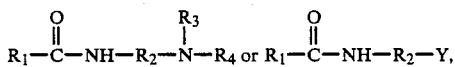

wherein $R_1$ is a fatty acid chain containing from about 11 to about 21 carbon atoms; $R_2$ is an alkylene group containing from two to about four carbon atoms; $R_3$ is hydrogen, a methyl group, an ethyl group or a hydroxyalkylene group containing from one to about three carbon atoms; $R_4$ is a methyl group, an ethyl group or a hydroxyalkylene group containing from one to about three carbon atoms; and Y is an organic heterocyclic nitrogen-containing moiety; from about 0.1% to about 2% by weight of a polydimethylsiloxane, wherein the polydimethylsiloxane is selected from the group consisting of a linear polydimethylsiloxane having a viscosity at 25° C. in the range from about 0.5 centistokes to about 5 centistokes and a boiling point at atmospheric pressure ranging from about 100° C. to about 250° C., a cyclic polydimethysiloxane having a viscosity at 25° C. of from about 2 to about 6 centistokes and a boiling point at atmospheric pressure ranging from about 170° C. to about 220° C., and combinations thereof; and a suitable liquid vehicle.

2. The hair-treating composition of claim 1 wherein the composition includes the water-soluble quaternary ammonium compound in an amount ranging from about 0.35% to about 5% by weight of the composition.

3. The hair-treating composition of claim 1 wherein the composition includes the water-soluble quaternary ammonium compound in an amount ranging from about 0.35% to about 3% by weight of the composition.

4. The hair-treating composition of claim 1 wherein the water-soluble quaternary ammonium compound includes a cation comprising at least one quaternary nitrogen atom and one or two long chain alkyl groups including from about 8 to about 18 carbon atoms.

5. The hair-treating composition of claim 4 wherein the quaternary nitrogen atom of the cation of the water-soluble quaternary ammonium compound includes one long chain alkyl group including from about 8 to about 18 carbon atoms as a substituent; and three substituents selected from the group consisting of a hydrogen atom, a methyl group, an ethyl group, a hydroxymethyl group, a hydroxyethyl group and combinations thereof.

6. The hair-treating composition of claim 4 wherein the quaternary nitrogen atom of the cation of the water-soluble quaternary ammonium compound includes two long chain alkyl groups including from about 8 to about 18 carbon atoms as substituents; and two substituents selected from the group consisting of a hydrogen atom, a methyl group, an ethyl group, a hydroxymethyl group, a hydroxyethyl group and combinations thereof.

7. The hair-treating composition of claim 4 wherein the quaternary nitrogen atom of the cation of the water-soluble quaternary ammonium compound includes one long chain alkyl group including from about 8 to about 18 carbon atoms as a substituent; one benzyl group as a substituent; and two substituents selected from the group consisting of a hydrogen atom, a methyl group, an ethyl group, a hydroxymethyl group, a hydroxyethyl group and combinations thereof.

8. The hair-treating composition of claim 4 wherein the quaternary nitrogen atom of the cation of the water-soluble quaternary ammonium compound includes two long chain alkyl groups including from about 8 to about 18 carbon atoms as a substituent; one benzyl group as a substituent; and one substituent selected from the group consisting of a hydrogen atom, a methyl group, an ethyl group, a hydroxymethyl group, a hydroxyethyl group and combinations thereof.

9. The hair-treating composition of claim 4 wherein the quaternary nitrogen atom of the cation of the water-soluble quaternary ammonium compound includes one long chain alkyl group including from about 8 to about 18 carbon atoms as a substituent; and one heterocyclic nitrogen-containing moiety as a substituent.

10. The hair-treating composition of claim 9, wherein the heterocyclic nitrogen-containing moiety is morpholine.

11. The hair-treating composition of claim 10 wherein the quaternary nitrogen atom of the cation of the water-soluble quaternary ammonium compound further includes a hydrogen atom, a methyl group, an ethyl group, a hydroxymethyl group or a hydroxyethyl group as a substituent.

12. The hair-treating composition of claim 9 wherein the heterocyclic nitrogen containing moiety is pyridine.

13. The hair-treating composition of claim 1 wherein the water-soluble quaternary ammonium compound includes an anion selected from the group consisting of chloride, methosulfate, ethosulfate and nitrate.

14. The hair-treating composition of claim 1 wherein the water-soluble quaternary ammonium compound is selected from the group consisting of laurtrimonium chloride; Quaternium-16; lauralkonium chloride; olealkonium chloride; dilauryldimonium chloride; cetalkonium chloride; dicetyldimonium chloride; laurylpyridinium chloride; cetylpyridinium chloride; soyatrimonium chloride; Polyquaternium-6; Polyquaternium-7; guarhydroxypropyltrimonium chloride; Polyquaternium-11; Polyquaternium-5; Polyquaternium-10; Polyquaternium-24; cetrimonium chloride; Quaternium-24; mytrimonium chloride; PEG-2 Cocomonium chloride; PEG-2 Cocoyl Quaternium-4; PEG-15 Cocoyl Quaternium-4; PEG-2 Stearyl Quaternium-4; Peg-15 Stearyl Quaternium-4; Peg-2 Oleyl Quaternium-4; PEG-15 Oleyl Quaternium-4; and combinations thereof.

15. The hair-treating composition of claim 15 wherein the water-soluble quaternary ammonium compound is selected from the group consisting of cetrimonium chloride, laurtrimonium chloride, Quaternium-16, laurylpyridinium chloride, mytrimonium chloride, Quaternium-24, soyatrimonium chloride, cetylpyridinium chloride, cetalkonium chloride, olealkonium chloride, dicetyldimonium chloride, lauralkonium chloride, Polyquaternium-11, and combinations thereof.

16. The hair-treating composition of claim 1 wherein the composition includes the oil-soluble quaternary ammonium compound in an amount ranging from about 0.4% to about 7% by weight of the composition.

17. The hair-treating composition of claim 1 wherein the oil-soluble quaternary compound includes a cation comprising at least one quaternary nitrogen atom and one or two long chain alkyl groups including from about 14 to about 22 carbon atoms.

18. The hair-treating composition of claim 17 wherein the quaternary nitrogen atom of the cation of the oil-soluble quaternary ammonium compound includes one long chain alkyl group including from about 14 to about 22 carbon atoms as a substituent; and three methyl groups, ethyl groups, or combinations thereof as substituents.

19. The hair-treating composition of claim 17 wherein the quaternary nitrogen atom of the cation of the oil-soluble quaternary ammonium includes two long chain alkyl groups including from about 14 to about 22 carbon atoms as a substituent; and two methyl groups, ethyl groups, or combinations thereof as substituents.

20. The hair-treating composition of claim 17 wherein the quaternary nitrogen atom of the cation of the oil-soluble quaternary ammonium compound includes one long chain alkyl group including from about 14 to about 22 carbon atoms as a substituent; one benzyl group; and two methyl groups, ethyl groups or combinations thereof as substituents.

21. The hair-treating composition of claim 17 wherein the quaternary nitrogen atom of the cation of the oil-soluble quaternary ammonium compound includes two long chain alkyl groups including from about 14 to about 22 carbon atoms as a substituent; one benzyl group; and one methyl group or ethyl group as a substituent.

22. The hair-treating composition of claim 17 wherein the quaternary nitrogen atom of the cation of the oil-soluble quaternary ammonium compound includes one long chain alkyl including from about 14 to about 22 carbon atoms as a substituent; and one organic heterocyclic nitrogen-containing moiety as a substituent.

23. The hair-treating composition of claim 22, wherein the heterocyclic nitrogen-containing moiety is morpholine.

24. The hair-treating composition of claim 23 wherein the quaternary nitrogen atoms of the cation of the oil-soluble quaternary ammonium compound further includes a methyl group or an ethyl group as a substituent.

25. The hair-treating composition of claim 24 wherein the heterocyclic nitrogen-containing moiety is pyridine.

26. The hair-treating composition of claim 1 wherein the oil-soluble quaternary ammonium compound includes an anion selected from the group consisting of chloride, bromide, methosulfate, ethosulfate, tosylate, acetate and phosphate.

27. The hair-treating composition of claim 1 wherein the oil-soluble quaternary ammonium compound is selected from the group consisting of cetethyldimonium bromide; cetrimonium tosylate; stearalkonium chloride; distearyldimonium chloride; Quaternium-18; cetrimonium bromide; cetethylmorpholinium ethosulfate; behenalkonium chloride; behentrimonium chloride; mytrimonium bromide; and combinations thereof.

28. The hair-treating composition of claim 1 wherein the oil-soluble quaternary ammonium compound is selected from the group consisting of distearyldimonium chloride, stearalkonium chloride, behenalkonium chloride, mytrimonium bromide, cetethylmorpholinium ethosulfate, and combinations thereof.

29. The hair-treating composition of claim 1 wherein the ratio of the water-soluble quaternary ammonium compound to the oil-soluble quaternary ammonium compound is in the range of about 0.1 to 1 to about 0.6 to 1.

30. The hair-treating composition of claim 1 wherein the ratio of the water-soluble quaternary ammonium compound to the oil-soluble quaternary ammonium compound is in the range of about 0.25 to 1 to about 0.45 to 1.

31. The hair-treating composition of claim 1 wherein the composition includes the acid-neutralized amidoamine in an amount ranging from about 0.1% to about 2% by weight of the composition.

32. The hair-treating composition of claim 1 wherein the amidoamine compound is selected from the group consisting of stearamidoethylethanolamine, stearamidoethyldiethanolamine, isostearamidopropylmorpholine, stearamidopropylmorpholine, stearamidopropyldimethylamine, diethylaminoethyl stearamide, dimethylaminopropyl myristamine, and combinations thereof.

33. The hair-treating composition of claim 1 wherein the amidoamine compound is neutralized with an acid selected from the group consisting of hydrochloric acid, sulfuric acid, nitric acid, phosphoric acid, lactic acid, tartaric acid, acetic acid, citric acid, gluconic acid, glycolic acid, propionic acid and combinations thereof.

34. The hair-treating composition of claim 1 wherein the acid-neutralized amidoamine is selected from the group consisting of stearamidoethylethanolamine phosphate, stearamidoethylethanolamine lactate, stearamidoethylethanolamine acetate, stearamidoethylethanolamine citrate, isostearamidoproylmorpholine phosphate, isostearamidopropylmorpholine lactate, isostearamidopropylmorpholine acetate, isostearamidopropylmorpholine citrate, stearamidopropylmorpholine phosphate, stearamidopropylmorpholine lactate, stearamidopropylmorpholine acetate, stearamidopropylmorpholine citrate, stearamidopropyldimethylamine phosphate, stearamidopropyldimethylamine lactate, stearamidopropyldimethylamine acetate, stearamidopropyldimethylamine citrate and combinations thereof.

35. The hair-treating composition of claim 1 wherein the composition includes the low molecular weight polydimethylsiloxane in an amount ranging from about 0.2% to about 1% by weight of the composition.

36. The hair-treating composition of claim 1 wherein the linear polydimethylsiloxane is selected from the group consisting of hexamethyldisiloxane, octamethyltrisoloxane, decamethyltetrasiloxane and combinations thereof.

37. The hair-treating composition of claim 1 wherein the cyclic polydimethylsiloxane is selected from the group consisting of hexamethylcyclotrisoloxane, ocatamethylcyclotetrasiloxane, decamethylcyclopentasiloxane, dodecamethylcyclohexasiloxane and combinations thereof.

38. The hair-treating composition of claim 1 wherein the suitable liquid vehicle comprises water.

39. The hair-treating composition of claim 38 wherein the liquid vehicle further comprises from about 1% to about 100% by weight relative to the total weight of the liquid vehicle of a lower alcohol, a polyol, a glycol, a glycol ether, or combinations thereof.

40. The hair-treating composition of claim 38 wherein the liquid vehicle further comprises from about 1% to about 100% by weight relative to the total weight of the liquid vehicle of ethyl alcohol, isopropyl alcohol, glycerol, 2-butoxyethanol, ethylene glycol, ethylene glycol monoethyl ether, propylene glycol, diethylene glycol monoethyl ether, diethylene glycol monomethyl ether or combinations thereof.

41. The hair-treating composition of claim 1 wherein the composition has a pH of from about 4 to about 7.

42. The hair-treating composition of claim 41 wherein the composition has a pH of from about 5.5 to about 6.5.

43. The hair-treating composition of claim 1 wherein the composition includes the water-soluble quaternary ammonium compound, the oil-soluble quaternary ammonium compound, the acid-neutralized amidoamine and the low molecular weight polydimethylsiloxane in a total amount ranging from about 1% to about 4% by weight of the composition.

44. The hair-treating composition of claim 1 wherein the composition includes the water-soluble quaternary ammonium compound, the oil-soluble quaternary ammonium compound, the acid-neutralized amidoamine and the low molecular weight polydimethylsiloxane in a combined maximum amount of about 3% by weight of the composition.

45. A method of treating hair comprising contacting the hair for sufficient time with a hair-treating composition comprising at least about 0.35% by weight of a water-soluble quaternary ammonium compound, wherein the water-soluble quaternary ammonium compound has the general structure:

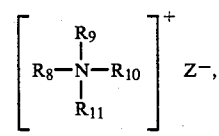

wherein $R_8$ is an alkyl group including from about 8 to about 18 carbon atoms; $R_9$ is selected from the group consisting of an alkyl group including from about 8 to about 18 carbon atoms, a hydrogen atom, a methyl group, an ethyl group, a hydroxymethyl group and a hydroxyethyl group; $R_{10}$ is selected from the group consisting of a benzyl group, a hydrogen atom, a methyl group, an ethyl group, a hydroxymethyl group and a hydroxyethyl group: $R_{11}$ is selected from the group consisting of a hydrogen atom, a methyl group, an ethyl group, a hydroxymethyl group and a hydroxyethyl group; and X is selected from the group consisting of chloride, methosulfate, ethosulfate and nitrate; from about 0.4% to about 15% by weight of an oil-soluble quaternary ammonium compound, wherein the oil-soluble quaternary ammonium compound has the general structure:

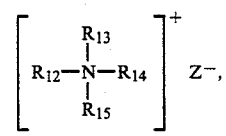

wherein $R_{12}$ is an alkyl group including from about 14 to about 22 carbon atoms; $R_{13}$ is selected from the group consisting of an alkyl group including from about 14 to about 22 carbon atoms, a methyl group and an ethyl group; $R_{14}$ is selected from the group consisting of a benzyl group, a methyl group and an ethyl group: $R_{15}$ is selected from the group consisting of a methyl group and an ethyl group; and Z is selected from the group consisting of chloride, bromide, methosulfate, ethosulfate, tosylate, acetate and phosphate; from about 0.1% to about 5% by weight of an acid-neutralized amidoamine, wherein the acid-neutralized amidoamine comprises an amidoamine compound having the general structure:

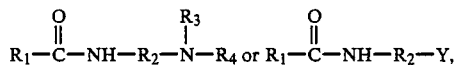

wherein $R_1$ is a fatty acid chain containing from about 11 to about 21 carbon atoms; $R_2$ is an alkylene group containing from two to about four carbon atoms; $R_3$ is hydrogen, a methyl group, an ethyl group or a hydroxyalkylene group containing from one to about three carbon atoms; $R_4$ is a methyl group, an ethyl group or a hydroxyalkylene group containing from one to about three carbon atoms; and Y is an organic heterocyclic nitrogen-containing moiety; from about 0.1% to about 2% by weight of a polydimethylsiloxane, wherein the polydimethylsiloxane is selected from the group consisting of a linear polydimethylsiloxane having a viscosity at 25° C. in the range from about 0.5 centistokes to about 5 centistokes and a boiling point at atmospheric pressure ranging from about 100° C. to about 250° C., a cyclic polydimethylsiloxane having a viscosity at 25° C. of from about 2 to about 6 centistokes and a boiling point at atmospheric pressure ranging from about 170° C. to about 220° C., and combinations thereof; and a suitable liquid vehicle.

46. A method of imparting conditioning properties to hair comprising contacting the hair for a sufficient time with a hair-treating composition comprising at least about 0.35% by weight of a water-soluble quaternary ammonium compound, wherein the water-soluble quaternary ammonium compound has the general structure:

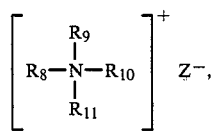

wherein $R_8$ is an alkyl group including from about 8 to about 18 carbon atoms; $R_9$ is selected from the group consisting of an alkyl group including from about 8 to about 18 carbon atoms, a hydrogen atom, a methyl group, an ethyl group, a hydroxymethyl group and a hydroxyethyl group; $R_{10}$ is selected from the group consisting of a benzyl group, a hydrogen atom, a methyl group, an ethyl group, a hydroxymethyl group and a hydroxyethyl group; $R_{11}$ is selected from the group consisting of a hydrogen atom, a methyl group, an ethyl group, a hydroxymethyl group and a hydroxyethyl group; and X is selected from the group consisting of chloride, methosulfate, ethosulfate and nitrate; from about 0.4% to about 15% by weight of an oil-soluble quaternary ammonium compound, wherein the oil-soluble quaternary ammonium compound has the general structure:

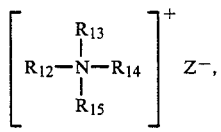

wherein $R_{12}$ is an alkyl group including from about 14 to about 22 carbon atoms; $R_{13}$ is selected from the group consisting of an alkyl group including from about 14 to about 22 carbon atoms, a methyl group and an ethyl group; $R_{14}$ is selected from the group consisting of a benzyl group, a methyl group and an ethyl group; $R_{15}$ is selected from the group consisting of a methyl group and an ethyl group; and Z is selected from the group consisting of chloride, bromide, methosulfate, ethosulfate, tosylate, acetate and phosphate; from about 0.1% to about 5% by weight of an acid-neutralized amidoamine, wherein the acid-neutralized amidoamine comprises an amidoamine compound having the general structure:

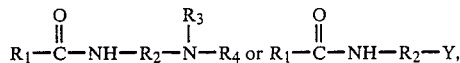

wherein $R_1$ is a fatty acid chain containing from about 11 to about 21 carbon atoms; $R_2$ is an alkylene group containing from two to about four carbon atoms; $R_3$ is hydrogen, a methyl group, an ethyl group or a hydroxyalkylene group containing from one to about three carbon atoms; $R_4$ is a methyl group, an ethyl group or a hydroxyalkylene group containing from one to about three carbon atoms; and Y is an organic heterocyclic nitrogen-containing moiety; from about 0.1% to about 2% by weight of a polydimethylsiloxane, wherein the polydimethylsiloxane is selected from the group consisting of a linear polydimethylsiloxane having a viscosity at 25° C. in the range from about 0.5 centistokes to about 5 centistokes and a boiling point at atmospheric pressure ranging from about 100° C. to about 250° C., a cyclic polydimethylsiloxane having a viscosity at 25° C. of from about 2 to about 6 centistokes and a boiling point at atmospheric pressure ranging from about 170° C. to about 220° C., and combinations thereof; and a suitable liquid vehicle.

47. The method of claim 46 further comprising rinsing the hair with water after contacting the hair with the hair-treating composition for a sufficient time.

48. A hair-treating composition comprising at least about 0.35% by weight of a water-soluble quaternary ammonium compound, wherein the water-soluble quaternary ammonium compound has the general structure:

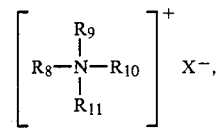

wherein $R_8$ is an alkyl including from about 8 to about 18 carbon atoms; $R_9$ is selected from the group consisting of an alkyl group including from about 8 to about 18 carbon atoms, a hydrogen atom, a methyl group, an ethyl group, a hydroxymethyl group and a hydroxyethyl group; $R_{10}$ is selected from the group consisting of a benzyl group, a hydrogen atom, a methyl group, an ethyl group, a hydroxymethyl group and a hydroxyethyl group; $R_{11}$ is selected from the group consisting of a hydrogen atom, a methyl group, an ethyl group, a hydroxymethyl group and a hydroxyethyl group; and X is selected from the group consisting of chloride, methosulfate, ethosulfate and nitrate; from about 0.4% to about 15% by weight of an oil-soluble quaternary ammonium compound, wherein the oil-soluble quaternary ammonium compound has the general structure:

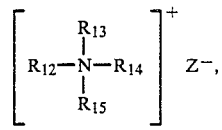

wherein $R_{12}$ is an alkyl group including from about 14 to about 22 carbon atoms; $R_{13}$ is selected from the group consisting of an alkyl group including from about 14 to about 22 carbon atoms, a methyl group and an ethyl group; $R_{14}$ is selected from the group consisting of a benzyl group, a methyul group and an ethyl group; $R_{15}$ is selected from the group consisting of a methyl group and an ethyl group; and Z is selected from the group consisting of chloride, bromide, methosulfate, ethosulfate, tosylate, acetate and phosphate, and wherein the ratio of the water-soluble quaternary ammonium compound to the oil-soluble quaternary ammonium compound is in the range of about 0.1 to 1 to about 0.6 to 1; from about 0.1% to about 5% by weight of an acid-neutralized amidoamine, wherein the acid-neutralized amidoamine comprises an amidoamine compound having the general structure.

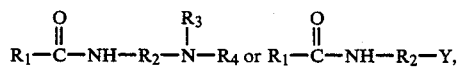

wherein $R_1$ is a fatty acid chain containing from about 11 to about 21 carbon atoms; $R_2$ is an alkylene group containing from two to about four carbon atoms; $R_3$ is hydrogen, a methyl group, an ethyl group or a hydroxyalkylene group containing from one to about three carbon atoms; $R_4$ is a methyl group, an ethyl group or a hydroxyalkylene group containing from one to about three carbon atoms; and Y is an organic heterocyclic nitrogen-containing moiety; from about 0.1% to about 2% by weight of a polydimethylsiloxane, wherein the polydimethylsiloxane is selected from the group consisting of a linear polydimethylsiloxane having a viscosity at 25° C. in the range from about 0.5 centistokes to about 5 centistokes and a boiling point at atmospheric pressure ranging from about 100° C. to about 250° C., a cyclic polydimethylsiloxane having a viscosity at 25° C. of from about 2 to about 6 centistokes and a boiling point at atmospheric pressure ranging from about 170° C. to about 220° C, and combinations thereof; and a suitable liquid vehicle.

49. A method of treating hair comprising contacting the hair for a sufficient time with a hair-treating composition comprising at least about 0.35% by weight of a water-soluble quaternary ammonium compound, wherein the water-soluble quaternary ammonium compound has the general structure:

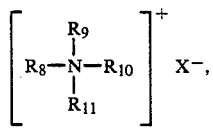

wherein $R_8$ is an alkyl group including from about 8 to about 18 carbon atoms; $R_9$ is selected from the group consisting of an alkyl group including from about 8 to about 18 carbon atoms, a hydrogen atom, a methyl group, an ethyl group, a hydroxymethyl group and a hydroxyethyl group; $R_{10}$ is selected from the group consisting of a benzyl group, a hydrogen atom, a methyl group, an ethyl group, a hydroxymethyl group and a hydroxyethyl group; $R_{11}$ is selected from the group consisting of a hydrogen atom, a methyl group, an ethyl group, a hydroxymethyl group and a hydroxyethyl group; and X is selected from the group consisting of chloride, methosulfate, ethosulfate and nitrate; from about 0.4% to about 15% by weight of an oil-soluble quaternary ammonium compound, wherein the oil-soluble quaternary ammonium compound has the general structure:

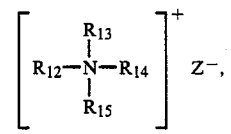

wherein $R_{12}$ is an alkyl group including from about 14 to about 22 carbon atoms; $R_{13}$ is selected from the group consisting of an alkyl group including from about 14 to about 22 carbon atoms, a methyl group and an ethyl group; $R_{14}$ is selected from the group consisting of a benzyl group, a methyl group and an ethyl group; $R_{15}$ is selected from the group consisting of a methyl group and an ethyl group; and Z is selected from the group consisting of chloride, bromide, methosulfate, ethosulfate, tosylate, acetate and phosphate, and wherein the ratio of the water-soluble quaternary ammonium compound to the oil-soluble quaternary ammonium compound is in the range of about 0.1 to 1 to about 0.6 to 1; from about 0.1% to about 5% by weight of an acid-neutralized amidoamine, wherein the acid-neutralized amidoamine comprises an amidoamine compound having the general structure:

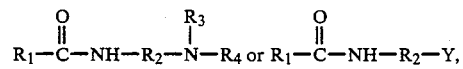

wherein $R_1$ is a fatty acid chain containing from about 11 to about 21 carbon atoms; $R_2$ is an alkylene group containing from two to about four carbon atoms; $R_3$ is hydrogen, a methyl group, an ethyl group or a hydroxyalkylene group containing from one to about three carbon atoms; $R_4$ is a methyl group, an ethyl group or a hydroxyalkylene group containing from one to about three carbon atoms; and Y is an organic heterocyclic nitrogen-containing moiety; from about 0.1% to about 2% by weight of a polydimethysiloxane, wherein the polydimethylsiloxane is selected from the group consisting of a linear polydimethylsiloxane having a viscosity at 25° C. in the range from about 0.5 centistokes to about 5 centistokes and a boiling point at atmospheric pressure ranging from about 100° C. to about 250° C, a cyclic polydimethylsiloxane having a viscosity at 25° C. of from about 2 to about 6 centistokes and a boiling point at atmospheric pressure ranging from about 170° C. to about 220° C., and combinations thereof; and a suitable liquid vehicle.

50. A hair-treating composition comprising at least about 0.35% by weight of a water-soluble quaternary ammonium compound, wherein the water-soluble quaternary ammonium compound has the general structure:

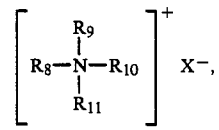

wherein $R_8$ is an alkyl group including from about 8 to about 18 carbon atoms; $R_9$ is selected from the group consisting of an alkyl group including from about 8 to about 18 carbon atoms, a hydrogen atom, a methyl group, an ethyl group, a hydroxymethyl group and a hydroxyethyl group; $R_{10}$ is selected from the group consisting of a benzyl group, a hydrogen atom, a methyl group, an ethyl group, a hydroxymethyl group and a hydroxyethyl group; $R_{11}$ is selected from the group consisting of a hydrogen atom, a methyl group, an ethyl group, a hydroxymethyl group and a hydroxyethyl group; and X is selected from the group consisting of chloride, methosulfate, ethosulfate and nitrate; from about 0.4% to about 15% by weight of an oil-soluble quaternary ammonium compound, wherein the oil-soluble quaternary ammonium compound has the general structure:

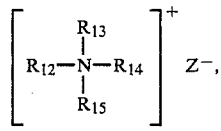

wherein $R_{12}$ is an alkyl group including from about 14 to about 22 carbon atoms; $R_{13}$ is selected from the group consisting of an alkyl group including from about 14 to about 22 carbon atoms, a methyl group and an ethyl group; $R_{14}$ is selected from the group consisting of a benzyl group, a methyl group and an ethyl group; $R_{15}$ is selected from the group consisting of a methyl group and an ethyl group; and Z is selected from the group consisting of chloride, bromide, methosulfate, ethosulfate, tosylate, acetate and phosphate, and wherein the ratio of the water-soluble quaternary ammonium compound to the oil-soluble quaternary ammonium compound is in the range of about 0.2 to 1 to about 0.6 to 1; from about 0.1% to about 5% by weight of an acid-neutralized amidoamine, wherein the acid-neutralized amidoamine comprises an amidoamine compound having the general structure:

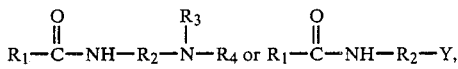

wherein $R_1$ is a fatty acid chain containing from about 11 to about 21 carbon atoms; $R_2$ is an alkylene group containing from two to about four carbon atoms; $R_3$ is hydrogen, a methyl group, an ethyl group or a hydroxyalkylene group containing from one to about three carbon atoms; $R_4$ is a methyl group, an ethyl group or a hydroxyalkylene group containing from one to about three carbon atoms; and Y is an organic heterocyclic nitrogen-containing moiety; from about 0.1% to about 2% by weight of a polydimethylsiloxane, wherein the polydimetnylsiloxane has a boiling point at atmospheric pressure ranging from about 100° C. to about 250° C.; and a suitable liquid vehicle.

* * * * *